US008877208B2

(12) United States Patent
Baker, Jr. et al.

(10) Patent No.: US 8,877,208 B2
(45) Date of Patent: Nov. 4, 2014

(54) MULTIVALENT NANOEMULSION VACCINES

(75) Inventors: James R. Baker, Jr., Ann Arbor, MI (US); Paul E. Makidon, Webberville, MI (US); Nicholas J. Mank, Ann Arbor, MI (US); Anna U. Bielinska, Ypsilanti, MI (US); Luz P. Blanco, Ann Arbor, MI (US); Jessica Knowlton, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 840 days.

(21) Appl. No.: 12/472,218

(22) Filed: May 26, 2009

(65) Prior Publication Data

US 2012/0107349 A1    May 3, 2012

Related U.S. Application Data

(60) Provisional application No. 61/055,818, filed on May 23, 2008.

(51) Int. Cl.
| | |
|---|---|
| A61K 39/116 | (2006.01) |
| A01N 63/00 | (2006.01) |
| A61K 45/00 | (2006.01) |
| A61K 39/00 | (2006.01) |
| A61K 39/38 | (2006.01) |
| A61K 39/02 | (2006.01) |
| A61K 39/08 | (2006.01) |
| A61K 39/07 | (2006.01) |
| A61K 9/107 | (2006.01) |
| A61K 39/29 | (2006.01) |
| A61K 39/39 | (2006.01) |

(52) U.S. Cl.
CPC ........... *A61K 39/292* (2013.01); *A61K 2039/57* (2013.01); *A61K 2039/543* (2013.01); *A61K 39/08* (2013.01); *C12N 2730/10134* (2013.01); *A61K 9/1075* (2013.01); *A61K 2039/55566* (2013.01); *A61K 39/0291* (2013.01); *A61K 39/39* (2013.01); *A61K 39/07* (2013.01)
USPC ................. 424/203.1; 424/93.3; 424/282.1; 424/184.1; 424/234.1; 424/239.1; 424/246.1; 424/247.1

(58) Field of Classification Search
None
See application file for complete search history.

(56) References Cited

U.S. PATENT DOCUMENTS

| | | | |
|---|---|---|---|
| 4,481,188 A | 11/1984 | Apontoweil et al. | |
| 4,596,792 A | 6/1986 | Vyas | |
| 4,599,230 A | 7/1986 | Milich | |
| 4,599,231 A | 7/1986 | Milich | |
| 4,601,903 A | 7/1986 | Frasch | |
| 4,895,452 A | 1/1990 | Yiournas et al. | |
| 4,895,454 A | 1/1990 | Kammleiter et al. | |
| 5,057,540 A | 10/1991 | Kensil | |
| 5,103,497 A | 4/1992 | Hicks | |
| 5,510,104 A | 4/1996 | Allen | |
| 5,547,677 A | 8/1996 | Wright | |
| 5,549,901 A | 8/1996 | Wright | |
| 5,571,531 A | 11/1996 | McDermott et al. | |
| 5,618,840 A | 4/1997 | Wright | |
| 5,662,957 A | 9/1997 | Wright | |
| 5,700,679 A | 12/1997 | Wright | |
| 5,716,637 A | 2/1998 | Anselem et al. | |
| 5,753,234 A | 5/1998 | Lee et al. | |
| 5,942,237 A | 8/1999 | Gizurarson et al. | |
| 5,951,988 A | 9/1999 | Littel-van den Hurk et al. | |
| 5,961,970 A | 10/1999 | Lowell et al. | |
| 6,005,099 A | 12/1999 | Davies | |
| 6,015,832 A | 1/2000 | Baker, Jr. et al. | |
| 6,350,784 B1 | 2/2002 | Squires | |
| 6,506,803 B1 | 1/2003 | Baker, Jr. et al. | |
| 6,558,695 B2 | 5/2003 | Luo et al. | |
| 6,559,189 B2 | 5/2003 | Baker, Jr. et al. | |
| 6,565,873 B1 | 5/2003 | Shefer et al. | |
| 6,627,198 B2 | 9/2003 | Reed et al. | |
| 6,635,676 B2 | 10/2003 | Baker, Jr. et al. | |
| 6,814,968 B1 | 11/2004 | Graham et al. | |
| 7,132,379 B2 | 11/2006 | Shanklin | |
| 7,314,624 B2 * | 1/2008 | Baker et al. ................ | 424/192.1 |
| 7,357,936 B1 | 4/2008 | Garcon | |

(Continued)

FOREIGN PATENT DOCUMENTS

| | | |
|---|---|---|
| EP | 0198474 | 10/1986 |
| EP | 0226846 | 7/1987 |

(Continued)

OTHER PUBLICATIONS

Anthrax overview, WebMD, 2011; http://www.webmd.com/cold-and-flu/tc/anthrax-topic-overview.*
Botulism, CDC, 2011; http://www.cdc.gov/nczved/divisions/dfbmd/diseases/botulism/.*
Gage et al., CDC-MMWR, 1996; 45(RR-14): 1-15.*
Claim set filed Sep. 16, 2011 for U.S. Appl. No. 11/929,275.*
Bowie et al. (Science, 1990, 257:1306-1310).*
Mims and Murphy, Parainfluenza Virus Sendai Infection in Macrophages, Ependyma, Choroid Plexus, Vascular Endothelium and Respiratory Tract of Mice, Am. J. Path., 70:315-324 (1973).
Mor et al., Perspective: edible vaccines—a concept coming of age, Trends Micrbiol 6:449-53 (1998).
Myc et al., Development of immune response that protects mice from viral pneumonitis after a single intranasal immunization with influenza A virus and nanoemulsion, Vaccine, Sep. 2003, vol. 21 (25-26), pp. 3801-3814.
Nabel, Challenges and opportunities of development of an AIDS vaccine. Nature, vol. 410, Apr. 2001, pp. 1002-1007.
Naughton et al., A rat model of infection by *Salmonella typhimurium* or Salm. enteritidis, J. Appl. Bact., 81:651-656 (1996).

(Continued)

*Primary Examiner* — Gary Nickol
*Assistant Examiner* — Lakia Tongue
(74) *Attorney, Agent, or Firm* — Tyler J. Sisk; Casimir Jones S.C.

(57) ABSTRACT

The present invention provides methods and compositions for the stimulation of immune responses. Specifically, the present invention provides methods of inducing an immune response against one or a plurality of pathogens (e.g., vaccinia virus, H5N1 influenza virus, *Bacillus anthracis, C. botulinum, Y. pestis*, Hepatitis B, and/or HIV, etc.) in a subject (e.g., a human subject) and compositions useful in such methods (e.g., immunogenic composition comprising nanoemulsion and one or a plurality of pathogens (e.g., inactivated by the nanoemulsion) and/or pathogen products and/or pathogen components). Compositions and methods of the present invention find use in, among other things, clinical (e.g. therapeutic and preventative medicine (e.g., vaccination)) and research applications.

19 Claims, 15 Drawing Sheets

(56) References Cited

U.S. PATENT DOCUMENTS

| | | | |
|---|---|---|---|
| 7,371,395 | B2 | 5/2008 | Parisot et al. |
| 7,767,216 | B2 | 8/2010 | Baker, Jr. et al. |
| 2001/0037100 | A1 | 11/2001 | Shanklin |
| 2002/0045667 | A1 | 4/2002 | Baker, Jr. et al. |
| 2002/0119207 | A1 | 8/2002 | Baker, Jr. et al. |
| 2002/0155084 | A1 | 10/2002 | Roessler et al. |
| 2003/0194412 | A1 | 10/2003 | Baker et al. |
| 2003/0202982 | A1 | 10/2003 | Birkett |
| 2004/0043041 | A1 | 3/2004 | Baker, Jr. et al. |
| 2005/0079185 | A1 | 4/2005 | Parisot et al. |
| 2005/0208083 | A1 | 9/2005 | Annis |
| 2005/0238660 | A1 | 10/2005 | Babiuk |
| 2005/0281843 | A1 | 12/2005 | Singh |
| 2006/0251684 | A1 | 11/2006 | Annis et al. |
| 2006/0257426 | A1* | 11/2006 | Baker et al. ............ 424/204.1 |
| 2006/0286124 | A1 | 12/2006 | Burt et al. |
| 2007/0036831 | A1 | 2/2007 | Baker, Jr. et al. |
| 2008/0039295 | A1 | 2/2008 | Steinmetz |
| 2008/0181949 | A1* | 7/2008 | Baker et al. ............ 424/484 |
| 2009/0123496 | A1 | 5/2009 | De-Heyder |
| 2009/0291095 | A1* | 11/2009 | Baker et al. ............ 424/184.1 |

FOREIGN PATENT DOCUMENTS

| | | |
|---|---|---|
| EP | 0278940 | 8/1988 |
| EP | 0299108 | 1/1989 |
| EP | 0304578 | 3/1989 |
| EP | 0468520 | 1/1992 |
| EP | 0549074 | 6/1993 |
| GB | 2122204 | 1/1984 |
| JP | H05-294845 | 11/1993 |
| JP | H10-500686 | 1/1998 |
| WO | 88/09336 | 12/1988 |
| WO | 91/14703 | 10/1991 |
| WO | 92/19265 | 11/1992 |
| WO | 93/13202 | 7/1993 |
| WO | 94/00153 | 1/1994 |
| WO | 94/21292 | 9/1994 |
| WO | 95-11700 | 5/1995 |
| WO | 95/14026 | 5/1995 |
| WO | 95/17210 | 6/1995 |
| WO | 96/02555 | 2/1996 |
| WO | 96/11711 | 4/1996 |
| WO | 96/33739 | 10/1996 |
| WO | 97-29773 | 8/1997 |
| WO | 98/16247 | 4/1998 |
| WO | 98/56414 | 12/1998 |
| WO | 99/10008 | 3/1999 |
| WO | 99/11241 | 3/1999 |
| WO | 99/12565 | 3/1999 |
| WO | 99-33459 | 7/1999 |
| WO | 2004-030608 | 4/2004 |
| WO | 2005-027872 | 3/2005 |

OTHER PUBLICATIONS

O'Hagan, D. Recent advances in Vaccine adjuvants for systemic and mucosal administration. J. Pharm. Pharmacol., 1997, vol. 49, 1-10.

Paul, Fundamental Immunology, Lippincott Williams & Wilkins Publishers; 5th edition Sep. 2003, p. 1353.

Perreault et al., Immunodominant minor histocompatibility antigens: the major ones, Immunol Today 19:69-74 (1998).

Portocala et al., Immunoelectrophoretic characterization of Sendai virus antigens, Virolegie 27:261-264 (1976).

Pouliot et al., Evaluation of the Role of LcrV?Toll-Like Receptor 2-Mediated Immunomodulation in the Virulence of *Yersinia pestis*, Infection and Immunity, 75(7): 3571-3580, Jul. 2007, p. 3578, col. 2, para 5; p. 3579, col. 1 para 1.

Richter and Kipp, Transgenic Plants as Edible Vaccines, Curr Top Microbiol Immunol 240:159-76 (1999).

Roberts, Resistance of Vaccinia Virus to Inactivation by Solvent/Detergent Treatment of Blood Products, Biologicals (2000) 28, 29-32.

Roy et al., Induction of antigen-specific CD8+ T cells, T helper cells, and protective levels of antibody in humans by particle-mediated administration of a hepatitis B virus DNA vaccine, Vaccine, 2001, vol. 19, p. 764-778.

Ruedl and Wolf, Features of Oral Immunization, Int. Arch. Immunol., 108:334 (1995).

Russell, Bacterial Spores and Chemical Sporicidal Agents, Clin. Micro. 3:99-119 (1990).

Sandusky et al., An Evaluation of Aureomycin and Chloromycetin in Experimental *Clostridium welchii* Infection, Surgery, 28:632-641 (1950).

Saraf et al., Lipid microparticles for mucosal immunization against hepatitis B, Vaccine. Jan. 9, 2006;24(1):45-56. Epub Aug. 8, 2005.

Sato et al., Immunostimulatory DNA sequences necessary for effective intradermal gene immunization, Science. Jul. 19, 1996;273(5273):352-4.

Schirmbeck et al., Immunization with soluble hepatitis B virus surface protein elicits murine H-2 class I-restricted CD8+ cytotoxic T lymphocyte responses in vivo, J Immunol. Feb. 1, 1994;152(3):1110-9.

Seeger, C. and Mason, W.S., Hepatitis B virus biology, Microbiol Mol Biol Rev. Mar. 2000;64(1):51-68.

Sercarz et al., Dominance and Crypticity of T Cell Antigenic Determinants, Anu Rev Immunol 11:729-766 (1993).

Silins et al., Development of Epstein-Barr Virus-specific Memory T Cell Receptor Clonotypes in Acute Infectious Mononucleosis, J Exp Med 184:1815-1824 (1996).

Steven et al., Epitope Focusing in the Primary Cytotoxic T Cell Response to Epstein-Barr Virus and Its Relationship to T Cell memory, J Exp Med 184:1801-1813 (1996).

Stevens et al., Comparison of Clindamycin, Rifampin, Tetracycline, metronidazole, and penicillin for Effiacy in Prevention of Experimental Gas Gangrene Due to *Clostridium perfringens*, J. Infect. Dis., 155:220-228 (1987).

Stevens et al., Comparison of Single and Combination Antimicrobial Agents for Prevention of Experimental Gas Gangrene Caused by *Clostridium perfringens*, Antimicrob. Agents Chemother., 31:312-316 (1987).

Takeuchi et al., Experimental Bacillary Dysentery: An Electron Microscopic Study of the Response of the intestinal Mucosa to Bacterial Invasion, Am. J. Pathol., 47:1011-1044 (1965).

Talaro, K. Foundations in Microbiology. 1993, Iowa: WmC Brown Communications, Inc.

Tiollais et. al., The hepatitis B virus, Nature. Oct. 10-16, 1985;317(6037):489-95.

Tremblay et al., T Lymphocyte Responses to Multiple Minor Histocompatibility Antigens Generate Both Self-Major Histocompatibility Complex-Restricted and Cross-Reactive Cytotoxic T Lymphocytes, Transplantation 58:59-67 (1994).

Tumpey et al., Mucosal delivery of inactivated influenza vaccine induces B-cell-dependent heterosubtypic cross-protection against lethal influenza A H5N1 virus infection. Journal of virology, Jun. 2001, vol. 75, No. 11, pp. 5141-5150.

Turner et al., Inactivated smallpox vaccine. A comparison of inactivation methods; J. Hyg., Camb., 1970, 68, p. 197.

Vaccine Design—the Subunit and Adjuvant Approach, edited by Powell and Newman, Plenum Press, New York, 1995.

van Ginkel et al., Enterotoxin-based mucosal adjuvants alter antigen trafficking and induce inflammatory responses in the nasal tract, Infect Immun. Oct. 2005;73(10):6892-902.

Van Herck et al., Long-term persistence of anti-HBs after vaccination with a recombinant DNA yeast-derived hepatitis B vaccine: 8-year results, Vaccine. Dec. 1998;16(20):1933-5.

Walker, B. D., and D. R Burton. May 9, 2008. Toward an AIDS vaccine. Science 320:760-764.

Weakly Epidemiological Record 1992, World Health Organization: Thirteenth meeting of the Global Advisory Group RPI. p. 1-8.

Weakly Epidemiological Record 1992, World Health Organization: Thirteenth meeting of the Global Advisory Group RPI. p. 9-16.

Welkos and Friedlander, comparative safety and efficacy against *Bacillus anthracis* of protective antigen and live vaccines in mice, Microb Pathog 5:127-139- (1988).

Welkos et al., Differences in Susceptibility of Inbred Mice to *Bacillus anthracis*, Infect Immun. 51:795-800 (1986).

(56) References Cited

OTHER PUBLICATIONS

Wieland et al., Intrahepatic induction of alpha/beta interferon eliminates viral RNA-containing capsids in hepatitis B virus transgenic mice, J Virol. May 2000;74(9):4165-73.

Woo et al., Hepatitis B surface antigen vector delivers protective cytotoxic T-lymphocyte responses to disease-relevant foreign epitopes, J Virol. Apr. 2006;80(8):3975-84.

Yanagita, Biochemical Aspects on the Germination of Conidiospores of *Aspergillus niger*, Arch Mikrobiol 26:329-344 (1957).

Zuckerman, Protective efficacy, immunotherapeutic potential, and safety of hepatitis B vaccines, J Med Virol. Feb. 2006;78(2):169-77.

Aguilar, J.C., et al., HCV core protein modulates the immune response against the HBV surface antigen in mice, Biochem Biophys Res Commun. Oct. 10, 2003;310(1):59-63.

Aguilar, J.C., et al., Development of a nasal vaccine for chronic hepatitis B infection that uses the ability of hepatitis B core antigen to stimulate a strong Th1 response against hepatitis B surface antigen, Immunol Cell Biol. Oct. 2004;82 (5):539-46.

Anttila, et al., Contribution of serotype-specific IgG concentration, IgG subclasses and relative antibody avidity to opsonophagocytic activity against *Streptococcus pneumoniae*, Clin Exp Immunol. Dec. 1999;118(3):402-7.

Assad, S. and A. Francis, Over a decade of experience with a yeast recombinant hepatitis B vaccine, Vaccine. Aug. 20, 1999;18(1-2):57-67.

Betancourt, A.A., et al., Phase I clinical trial in healthy adults of a nasal vaccine candidate containing recombinant hepatitis B surface and core antigens, Int J Infect Dis. Sep. 2007;11(5):394-401. Epub Jan. 24, 2007.

Brazolot-Millan et al., CpG DNA can induce strong Th1 humoral and cell-mediated immune responses against hepatitis B surface antigen in young mice, Proc Natl Acad Sci U S A. Dec. 22, 1998;95(26):15553-8.

Centers for Disease Control and Prevention (CDC), Global progress toward universal childhood hepatitis B vaccination, MMWR Morb Mortal Wkly Rep. Sep. 12, 2003;52(36):868-70.

Chen, H., Recent advances in mucosal vaccine development, J Control Release. Jul. 3, 2000;67(2-3):117-28.

Chisari, F.V. and C. Ferrari, Hepatitis B Virus Immunopathogenesis, Ann. Rev. Immunol, 1995. 13(1): p. 29-60.

Davis et al., CpG DNA is a potent enhancer of specific immunity in mice immunized with recombinant hepatitis B surface antigen, J Immunol. Jan. 15, 1998;160(2):870-6.

Debin, A., et al., Intranasal immunization with recombinant antigens associated with new cationic particles induces strong mucosal as well as systemic antibody and CTL responses, Vaccine. Jun. 21, 2002;20(21-22):2752-63.

Donovan et al., Prevention of murine influenza a virus pneumonitis by surfactant nano-emulsions, Antiviral Chemistry & Chemotherapy 2000; 11:41-49.

Easterday et al., Use of single nucleotide polymorphisms in the plcR gene for specific identification of *Bacillus anthracis*, J Clin Microbiol. Apr. 2005;43(4):1995-7.

Farchaus, J., et al., Fermentation, purification, and characterization of protective antigen from a recombinant, avirulent strain of *Bacillus anthracis*, Appl Environ Microbiol. Mar. 1998;64(3):982-91.

Floreani, A., et al., Long-term persistence of anti-HBs after vaccination against HBV: an 18 year experience in health care workers, Vaccine, vol. 22, Issues 5-6, Jan. 26, 2004, pp. 608-611.

Gesemann, M. and N. Scheiermann, Quantification of hepatitis B vaccine-induced antibodies as a predictor of anti-HBs persistence, Vaccine. Apr. 1995;13(5):443-7.

Gherardi, R.K., et al., Macrophagic myofasciitis lesions assess long-term persistence of vaccine-derived aluminium hydroxide in muscle, Brain. Sep. 2001;124(Pt 9):1821-31.

Gilbert, R.J.C., et al., Hepatitis B small surface antigen particles are octahedral, Proc Natl Acad Sci U S A. Oct. 11, 2005;102(41):14783-8. Epub Oct. 3, 2005.

Graham BS (2006) New Approaches to Vaccine Adjuvants: Inhibiting the Inhibitor. PLoS Med 3(1): e57.

Gupta, R.K., Aluminum compounds as vaccine adjuvants, Adv Drug Deliv Rev. Jul. 6, 1998;32(3):155-172.

Hamouda and Baker, Antimicrobial mechanism of action of surfactant lipid preparations in enteric Gram-negative bacilli, J Appl Microbiol. Sep. 2000;89(3):397-403.

Hamouda et al., A novel surfactant nanoemulsion with broad-spectrum sporicidal activity against Bacillus species, J Infect Dis. Dec. 1999;180(6):1939-49.

Hepatitis B Fact sheet No. 204. 2000, World Health Organization.

Hilgers et al., Synergistic effects of synthetic adjuvants on the humoral immune response, Int Arch Allergy Appl Immunol. 1986;79(4):392-6.

Hilgers et al., Synthetic sulpholipopolysaccharides: novel adjuvants for humoral immune responses, Immunology. Jan. 1987;60(1):141-6.

Hilleman, M.R., Overview of the pathogenesis, prophylaxis and therapeusis of viral hepatitis B, with focus on reduction to practical applications, Vaccine. Feb. 28, 2001;19(15-16):1837-48.

Isaka, M., et al., Mucosal immunization against hepatitis B virus by intranasal co-administration of recombinant hepatitis B surface antigen and recombinant cholera toxin B subunit as an adjuvant, Vaccine. Jan. 8, 2001;19 (11-12):1460-6.

Jaganathan, K.S. and S.P. Vyas, Strong systemic and mucosal immune responses to surface-modified PLGA microspheres containing recombinant hepatitis B antigen administered intranasally, Vaccine. May 8, 2006;24 (19):4201-11. Epub Jan. 18, 2006.

Kensil et al., Separation and characterization of saponins with adjuvant activity from *Quillaja saponaria* Molina cortex, J Immunol. Jan. 15, 1991;146(2):431-7.

Kensil, Saponins as vaccine adjuvants, Crit Rev Ther Drug Carrier Syst. 1996;13(1-2):1-55.

Khajuria, A., et al., A new vaccine adjuvant (BOS 2000) a potent enhancer mixed Th1/Th2 immune responses in mice immunized with HBsAg, Vaccine. Jun. 6, 2007;25(23):4586-94. Epub Apr. 23, 2007.

Lambert, P.-H. et al., Can successful vaccines teach us how to induce efficient protective immune responses?, Nat Med. Apr. 2005;11(4 Suppl):S54-62.

Lemon, S.M. and D.L. Thomas, Vaccines to prevent viral hepatitis, N Engl J Med. Jan. 16, 1997;336(3):196-204.

Leroux-Roels, G., et al., Correlation between in vivo humoral and in vitro cellular immune responses following immunization with hepatitis B surface antigen (HBsAg) vaccines, Vaccine. Jul. 1994;12(9):812-8.

Lobaina, Y., et al., Mucosal immunogenicity of the hepatitis B core antigen, Biochem Biophys Res Commun. Jan. 17, 2003;300(3):745-50.

McClary, H., et al., Relative sensitivity of hepatitis B virus and other hepatotropic viruses to the antiviral effects of cytokines, J Virol. Mar. 2000;74(5):2255-64.

McCluskie, M.J. and H.L. Davis, CpG DNA is a potent enhancer of systemic and mucosal immune responses against hepatitis B surface antigen with intranasal administration to mice, J Immunol. Nov. 1, 1998;161(9):4463-6.

Mosmann and Coffman, TH1 and TH2 cells: different patterns of lymphokine secretion lead to different functional properties, Annu Rev Immunol. 1989;7:145-73.

Mutsch et al., Use of the inactivated intranasal influenza vaccine and the risk of Bell's palsy in Switzerland, N Engl J Med. Feb. 26, 2004;350(9):896-903.

Neutra, M.R. and P.A. Kozlowski, Mucosal vaccines: the promise and the challenge, Nat Rev Immunol. Feb. 2006;6(2):148-58.

Park et al., Two subtypes of hepatitis B virus-associated glomerulonephritis are associated with different HLA-DR2 alleles in Koreans, Tissue Antigens. Dec. 2003;62(6):505-11.

Payette, P., et al., Testing of CpG-optimized protein and DNA vaccines against the hepatitis B virus in chimpanzees for immunogenicity and protection from challenge, Intervirology. 2006;49(3):144-51.

Peterson, The structure of hepatitis B surface antigen and its antigenic sites, Bioessays. Jun. 1987;6(6):258-62.

Pittman, Aluminum-containing vaccine associated adverse events: role of route of administration and gender, Vaccine. May 31, 2002;20 Suppl 3:S48-50.

(56) References Cited

OTHER PUBLICATIONS

Altemeier et al., Chloromycetin and Aureomycin in Experimental Gas Gangrene, Surgery, 28:621-631 (1950).
Baker Jr., et al., Enhanced systemic and mucosal immune responses in mice immunized with recombinant *Bacillus anthracis* protective antigen (rPA) using a novel nanoemulsion adjuvant, Journal of Allergy and Clinical Immunology, vol. 113, No. 2 Supplement, Feb. 2004, p. S292 XP 002560178 & 60th Annual Meeting of the American Academy of Allergy, Asthma and Immunology (AAAAI); San Francisco, CA, USA; Mar. 19-23, 2004.
Baldwin et al., Characterization of the Antibody Response to the Receptor Binding Domain of Botulinum Neurotoxin Serotypes A and E, infection and Immunity, 73(10): 6998-7005, Oct. 2005, p. 6999, col. 1, para 2: p. 7004, col. 1, para 3.
Bende et al., Update: Search for an AIDS vaccine. AIDS Read, 10(9), 2000, pp. 526-537.
Bielinska et al., A Novel, Killed-Virus Nasal vaccinia Virus Vaccine, clinical and Vaccine Immunology, Feb. 2008, p. 348-358.
Bielinska et al., Mucosal immunization with a novel nanoemulsion-based recombinant anthrax protective antigen vaccine protects against *Bacillus anthracis* spore challenge. Infection and Immunity. Aug. 2007, vol. 75, No. 8, 4020-4029.
Brown et al., Differential Diagnosis of *Bacillus cereus, Bacillus anthracis*, and *Bacillus cereus* Var. Mycoides, J. Bact., 75:499-509 (1958).
Burdon and Wende, On the Differentiation of Anthrax Bacilli from *Bacillus cereus*, J Infect. Diseas. 170(2):224-34 (1960).
Burdon et al., Experimental Infection of Mice with *Bacillus cereus*: Studies of Pathogenesis and Pathologic Changes, J Infect. Diseas. 117:307-316 (1967).
Burton, D. R, et al. 2004. HIV vaccine design and the neutralizing antibody problem. Nat. Immunol. 5(3):233-236.
Butterton et al., Development of a Germfree Mouse Model of Vibrio cholerae Infection, Infect. Immun., 64:4373-4377 (1996).
Carter and Collins, The Route of Enteric Infection in Normal Mice, J. Exp. Med., 139:1189-1203 (1974).
Castleman et al., Pathogenesis of Bronchiolitis and Pneumonia Induced in neonatal and Weanling Rats by Parainfluenza (Sendai) Virus, Am. J. Path., 129:277-286 (1987).
Castleman, Respiratory tract lesions in weanling outbred rats infected with Sendai virus, Am. J. Vet. Res., 44:1024-1031 (1983).
Collins and Carter, Comparative Immunogenicity of Heat-Killed and Living Oral *Salmonella* Vaccines, Infect. Immun., 6:451-458 (1972).
Collins, Salmonellosis in Orally Infected Specific Pathogen-Free C557B1 Mice, Infect. Immun., 5:191-198 (1972).
Connick, E., et al. 2007. CTI fail to accumulate at sites of HIV-1 replication in lymphoid tissue. J. Immunol. 178:6975-6983.
Cox et al., Influenza virus: immunity and vaccination strategies, comparison of the immune response to inactivated and live, attenuated influenza vaccines. Scandinavian Journal of Immunology, vol. 59, p. 1-15, 2004.
Desrosiers, Prospects for an AIDS vaccine. Nature Medicine, vol. 10(3), Mar. 2004, pp. 221-223.
Drobniewski, *Bacillus cereus* and Related Species, Clin. Microbio. Rev. 6:324-338 (1993).
Eriksson et al., Virus validation of plasma-derived products produced by Pharmacia, with particular reference to immunoglobulins, Blood Coagulation and Fibtinolysis 5 (Suppl. 3):S37-S44 (1994).
Feinberg et al., AIDS vaccine models: challenging challenge viruses. Nature Medicine, vol. 8 (3), Mar. 2002, pp. 207-210.
Fields, Fields Virology, (Knipe, Howley (editors)), Lippincott Williams & Wilkins Publishers; Aug. 2001, p. 1555.
Finkelstein et al., Pathogenesis of Experimental Cholera in Infant Rabbits, J. Infect. Dis., 114:203-216 (1964).
Formal et al., Role of the Small intestine in an Experimental infection in Guinea Pigs, J. Bact. 85:119-125 (1963).
Freter, Experimental Enteric Shigella and Vibrio Infections in Mice and Guinea Pigs, J. Exp. Med., 104:411-418 (1956).
Freter, The Fatal Enteric Cholera Infection in the Guinea Pig, Achieved by Inhibition of Normal Enteric Flora, J. Infect. Dis., 97:57-65 (1955).
Fritz et al., Pathology of Experimental Inhalation Anthrax in the Rhesus Monkey, Lab. Invest. 73:691-702 (1995).
Gallo, R C. 2005. The end or the beginning of the drive to an HIV-preventive vaccine: a view from over 20 years. The lancet 366: 1894-1898.
Halvorson and Church, Biochemistry of Spores of Aerobic Bacilli with Special Reference to Germination, Bacteriol Rev. 21:112-131 (1957).
Hamouda T Et al: "A Novel Surfactant Nanoemulsion with a unique non-irritant topical antimicrobial activity against bacteria, enveloped viruses and fungi" Microbiological Research vol. 156, No. 1, Jan. 1, 2001, pp. 1-07.
Hills, Chemical Factors in the Germination of Spore-bearing Aerobes: observations on the Influence of Species, Strain and Conditions of Growth, J. Gen. Micro. 4:38-47 (1950).
Horowitz et al., Solvent/Detergent-Treated Plasma: A Virus-Inactivated Substitute for Fresh Frozen Plasma, Blood 79:826-831 (1992).
Jacoby et al., Sendai Viral Pneumonia in Aged BALB/c Mice, Exp. Gerontol., 29:89-100 (1994).
Johnson et al., Age-dependent Resistance to Viral Encephalitis: Studies of Infections Due to Sindbis Virus in Mice, J. Infect. Dis., 125:257-262 (1972).
Johnson et al., Virus Invasion of the Central Nervous System, Am. J. Path., 46:929-943 (1965).
Karaivanova and Spiro, Sulphation of N-linked oligosaccharides of vesicular stomatitis and influenza virus envelope blycoproteins: host cell specifity, subcellular localization and identification of substituted saccharides, Biochem J. 329(Pt 3):511-518 (1998).
Klausner et al., The need for a global HIV vaccine enterprise. Science, vol. 300, Jun. 2003, pp. 2036-2039.
Labrec et al., Epithelial Cell Penetration as an Essential Step in the Pathogenesis of Bacillary Dysentery, J. Bact. 88:1503-1518 (1964).
Lamanna and Jones, Lethality for Mice of Vegetative and Spore Forms of *Bacillus cereus* and *Bacillus cereus*-Like Insect Pathogens Injected intraperitoneally and Subcutaneously, J. Bact. 85:532-535 (1963).
Lee, Chapter 32 AIDS Vaccines: 32.1 Acquired immunodeficiency disease vaccines: design and development. AIDS: Bioloğhy, Diagnosis, Treatment, and Prevention, fourth edition, edited by DeVitat, Jr. et al., Lippincott-Raven, 1997, pp. 605-616.
Levine et al., New Knowledge on Pathogenesis of Bacterial Enteric Infections as Applied to Vaccine Development, Microbiol. Rev., 47:510-550 (1983).
Maha and Igarashi, The Effect of Nonionic Detergent on Dengue and Japanese Encephalitis Virus Antigens in Antigen Detection Elisa and IgM-Capture Elisa, Southeast Asian J. Trop. Med. Pub. Health 28:718-722 (1997).
Mammen et al., Effective Inhibitors of Hemagglutination by Influenza Virus Synthesized from Plymers Having Active Ester Groups. insight into Mechanism of Inhibition, J Med Chem 38:4179-4190 (1995).
Massion et al., Parainfluenza (Sendai) Virus Infects Ciliated Cells and Secretory Cells but Not Basal Cells of Rat Tracheal Epithelium, Am. J. Respir. Cell Mol. Biol. 9:361-370 (1993).
McMichael, Cytotoxic T Lymphocytes Specific for Influenza Virus, Curr. Top. Microbiol. Immunol. 189:75-91 (1994).
Akira et al., Pathogen recognition and innate immunity, Cell. Feb. 24, 2006;124(4):783-801.
Bielinska et al., Nasal Immunization with a Recombinant HIV gp 120 and Nanoemulsion Adjuvant Produces Th1 Polarized Responses and neutralizing Antibodies to Primary HIV Type I Isolates. AIDS Research and Human Retroviruses, Feb. 2008, vol. 24(2), pp. 271-281; Abstract, Fig. 1E; p. 272, para 5; p. 275, para 3, 5; p. 278, para 3; p. 279, para 1.
de Waal et al., Moderate local and systemic respiratory syncytial virus-specific T-cell responses upon mild or subclinical RSV infection, J Med Virol. Jun. 2003;70(2):309-18.
Earl et al, Immunogenicity of a highly attenuated MVA smallpox vaccine and protection against monkeypox, Nature. Mar. 11, 2004;428(6979):182-5.

(56) References Cited

OTHER PUBLICATIONS

Edghill-Smith et al., Smallpox vaccine-induced antibodies are necessary and sufficient for protection against monkeypox virus, Nat Med. Jul. 2005;11(7):740-7. Epub Jun. 12, 2005.
Greenberg et al, Safety and immunogenicity of new cell-cultured smallpox vaccine compared with calf-lymph derived vaccine: a blind, single-centre, randomised controlled trial, Lancet. Jan. 29-Feb. 4, 2005;365(9457):398-409.
Hammarlund et al., Duration of antiviral immunity after smallpox vaccination, Nat Med. Sep. 2003;9(9):1131-7. Epub Aug. 17, 2003.
Hershey, IL-13 receptors and signaling pathways: an evolving web, J Allergy Clin Immunol. Apr. 2003;111(4):677-90; quiz 691.
Kool et al., Alum adjuvant boosts adaptive immunity by inducing uric acid and activating inflammatory dendritic cells, J Exp Med. Apr. 14, 2008;205(4):869-82. Epub Mar. 24, 2008.
Lukacs et al., Differential immune responses and pulmonary pathophysiology are induced by two different strains of respiratory syncytial virus, Am J Pathol. Sep. 2006;169(3):977-86.
Sigurs et al., Clinical perspectives on the association between respiratory syncytial virus and reactive airway disease, Respir Res. 2002;3 Suppl 1:S8-14. Epub Jun. 24, 2002.
Triantafilou & Triantafilou, Lipopolysaccharide recognition: CD14, TLRs and the LPS-activation cluster, Trends Immunol. Jun. 2002;23(6):301-4.
Baker, Jr. et al., Nasal immunization with a novel nanoemulsion adjuvant modifies Th2-polarized immune responses, Journal of Allergy and Clinical Immunology, vol. 121, No. 3, Mar. 2008, p. 796 & 64th Annual Meeting of the American-Academy-of-Allergy-Asthma-and-Immunology, Philadelphia, PA, USA, Mar. 14-18, 2008.

\* cited by examiner

FIGURE 1

PAGE analysis of recombinant PA, HCR/A, LcrV and LcrV10 proteins

Lane:
1 - PA
2 - HCR/A1
3 - LcrV
4 - LcrV10
M - MW marker

Time course of serum antibody response in mice intranasally immunized with trivalent vaccine containing LcrV10 antigen

Time course of serum antibody response in mice intranasally immunized with trivalent vaccine containing LcrV antigen Trivalent [HCR/A1+PA+LcrV] - NE — anti-HCR/A1
— anti-PA
— anti-LcrV

Anti-PA IgG

B

Anti-HCR/A1 IgG

Anti-LcrV and LcrV10 IgG

Figure 6

Trivalent [LcrV mix]-NE (Bar chart: Fold stimulation vs IFN-gamma, IL-4, IL-10; bars for rPA, rLcrV, HCR/A1. IFN-gamma: rPA ~15, rLcrV ~5, HCR/A1 ~3. IL-4 and IL-10 near 1.)

Trivalent [LcrV10 mix]-NE (Bar chart: Fold stimulation vs IFN-gamma, IL-4, IL-10; bars for rPA, rLcrV10, HCR/A1. IFN-gamma: rPA ~8, rLcrV10 ~5, HCR/A1 ~3. IL-4 and IL-10 near 1.)

**Intranasal challenge with ~150 LD$_{50}$ of *Yersinia pestis* C092**

20 μg antigen dose

- LcrV-20% NE
- LcrV-5% NE
- LcrV10-20% NE
- LcrV10-5% NE
- LcrV or V10- Alum
- 20% NE
- Naïve

FIGURE 11

**Intranasal challenge with ~150 LD$_{50}$ of *Yersinia pestis* C092**

10 μg antigen dose

- LcrV-20% NE
- LcrV-5% NE
- LcrV10-20% NE
- LcrV10-5% NE
- naive

MULTIVALENT NANOEMULSION VACCINES

CROSS-REFERENCE TO RELATED APPLICATIONS

This application claims priority to U.S. Provisional Patent Application Ser. No. 61/055,818, filed 23 May 2008, hereby incorporated by reference in its entirety.

FIELD OF THE INVENTION

The present invention provides methods and compositions for the stimulation of immune responses. Specifically, the present invention provides methods of inducing an immune response against one or a plurality of pathogens (e.g., vaccinia virus, H5N1 influenza virus, *Bacillus anthracis, C. botulinum, Y. pestis*, Hepatitis B, and/or HIV, etc.) in a subject (e.g., a human subject) and compositions useful in such methods (e.g., immunogenic composition comprising nanoemulsion and one or a plurality of pathogens (e.g., inactivated by the nanoemulsion) and/or pathogen products and/or pathogen components). Compositions and methods of the present invention find use in, among other things, clinical (e.g. therapeutic and preventative medicine (e.g., vaccination)) and research applications

BACKGROUND

Immunization is a principal feature for improving the health of people. Despite the availability of a variety of successful vaccines against many common illnesses, infectious diseases remain a leading cause of health problems and death. Significant problems inherent in existing vaccines include the need for repeated immunizations, and the ineffectiveness of the current vaccine delivery systems for a broad spectrum of diseases.

In order to develop vaccines against pathogens that have been recalcitrant to vaccine development, and/or to overcome the failings of commercially available vaccines due to expense, complexity, and underutilization, new methods of antigen presentation must be developed which will allow for fewer immunizations, more efficient usage, and/or fewer side effects to the vaccine.

SUMMARY OF THE INVENTION

The present invention provides methods and compositions for the stimulation of immune responses. Specifically, the present invention provides methods of inducing an immune response against one or a plurality of pathogens (e.g., vaccinia virus, H5N1 influenza virus, *Bacillus anthracis, C. botulinum, Y. pestis*, Hepatitis B, and/or HIV, etc.) in a subject (e.g., a human subject) and compositions useful in such methods (e.g., immunogenic composition comprising nanoemulsion and one or a plurality of pathogens (e.g., inactivated by the nanoemulsion) and/or pathogen products and/or pathogen components). Compositions and methods of the present invention find use in, among other things, clinical (e.g. therapeutic and preventative medicine (e.g., vaccination)) and research applications.

Accordingly, in some embodiments, the present invention provides a composition comprising a vaccine, the vaccine comprising an emulsion and a plurality of immunogens, the emulsion comprising an aqueous phase, an oil phase, and a solvent. In some embodiment, the plurality of immunogens comprises a plurality of pathogens (e.g., an inactivated pathogens). In other embodiments, the plurality of immunogens comprises a plurality pathogen compoenents and/or products (e.g., including, but not limited to, a protein, peptide, polypeptide, nucleic acid, polysaccharide, or a membrane component derived from the pathogens). In some embodiments, the immunogens and the emulsion are combined in a single vessel.

The present invention is not limited to any particular immunogens. For example, multiple immunogens may be used in the present invention including, but not limited to, those described herein (e.g., protective antigen (PA), gp160, gp41, Tat, Nef, lethal factor, edema factor, protective antigen degradation products, etc.). Similarly, the present invention is not limited by the type of disease from which a subject is protected. Indeed, a subject can be protected from a variety of diseases including, but not limited to, AIDS, the plague, disease caused by hepatitis virus, smallpox and anthrax. In some embodiments, immunity protects the subject from challenge with a subsequent exposure to live pathogen (e.g., HIV, vaccinia virus, *B. anthracis*, hepatitis virus (e.g., hepatitis B virus, hepatitis A virus, hepatitis C virus, etc.), *Yersinia pestis, Clostridium botulinum*, etc.).

In certain embodiments, the immunogen is selected from the group consisting of virus, bacteria, fungus and pathogen products derived from the virus, bacteria, or fungus. The present invention is not limited to a particular virus. A variety of viral immunogens are contemplated including, but not limited to, influenza A virus, avian influenza virus, H5N1 influenza virus, West Nile virus, SARS virus, Marburg virus, Arenaviruses, Nipah virus, alphaviruses, filoviruses, herpes simplex virus I, herpes simplex virus II, sendai virus, sindbis virus, vaccinia virus, parvovirus, human immunodeficiency virus, hepatitis B virus, hepatitis C virus, hepatitis A virus, cytomegalovirus, human papilloma virus, picornavirus, hantavirus, junin virus, and ebola virus. The present invention is not limited to a particular bacteria. A variety of bacterial immunogens are contemplated including, but not limited to, *Bacillus cereus, Bacillus circulans* and *Bacillus megaterium, Bacillus anthracis*, bacterial of the genus *Brucella, Vibrio cholera, Coxiella burnetii, Francisella tularensis, Chlamydia psittaci, Ricinus communis, Rickettsia prowazekii*, bacteria of the genus *Salmonella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia pestis, Yersinia enterocolitica*, and *Yersinia pseudotuberculosis*. The present invention is also not limited to a particular fungus. A variety of fungal immunogens are contemplated including, but not limited to, *Candida* and *Aspergillus*.

In some embodiments, the present invention provides a method of inducing an immune response to a plurality of immunogens (e.g., two or more (e.g., three, four, five, six, seven, eight, or more immunogens) derived from a plurality of environmental pathogens (e.g., those described herein))) in a subject, comprising providing a nanoemulsion; and a plurality of immunogens; combining the nanoemulsion with the immunogens; and administering the combined nanoemulsion and immunogens to the subject under conditions such that the subject produces an immune response to the immunogens. In some embodiments, administrating comprises mucosal administration. In some embodiments, inducing an immune response induces immunity to each of the plurality of immunogens in the subject. In some embodiments, inducing an immune response to the immunogens induces immunity to the plurality of pathogens from which the immunogens are derived. In some embodiments, immunity comprises systemic immunity. In some embodiments, immunity comprises mucosal immunity. In some embodiments, the immune response comprises increased expression of IFN-γ in the subject. In some embodiments, the immune response comprises increased expression of TNF-α in the subject. In some embodiments, the immune response comprises a systemic IgG response to the immunogens. In some embodiments, the immune response comprises a mucosal IgA response to the immunogens. In some embodiments, the composition comprises between 15 and 75 μg of a recombinant immunogen. The present invention is not limited to this amount of immunogen. Indeed, a variety of doses of immunogen are contemplated to be useful in the present invention. In some embodiments, a composition comprising a plurality of immunogens utilized to induce an immune response to a plurality of immunogens and/or environmental pathogens comprises two or more immunogens from virus, bacteria, fungus and pathogen products derived from one or more viruses, bacteria, or fungi. In some embodiments, the immunogens are combined (e.g., in any ratio) to optimize protection against environmental pathogens from which the immunogens are derived.

The present invention further provides a kit comprising a vaccine, the vaccine comprising an emulsion and one or more immunogens, the emulsion comprising an aqueous phase, an oil phase, and a solvent. In some embodiments, the kit further comprises instructions for using the kit for vaccinating a subject against the one or more immunogens.

In some embodiment, the one or more immunogens comprise a pathogen (e.g., an inactivated pathogen). In other embodiments, the immunogens comprise one or more pathogen products (e.g., including, but not limited to, a protein, peptide, polypeptide, nucleic acid, polysaccharide, or membrane component derived from the pathogen). In some embodiments, the one or more immunogens and the emulsion are combined in a single vessel.

In still further embodiments, the present invention provides a method of inducing immunity to one or more immunogens, comprising providing an emulsion comprising an aqueous phase, an oil phase, and a solvent; and one or more immunogens; combining the emulsion with the one or more immunogens to generate a vaccine composition; and administering the vaccine composition to a subject. In some embodiments, administering comprises contacting the vaccine composition with a mucosal surface of the subject. For example, in some embodiments, administering comprises intranasal administration. In some preferred embodiments, the administering occurs under conditions such that the subject generates immunity to the one or more immunogens (e.g., via generating humoral immune responses to the one or more immunogens).

In some embodiment, the one or more immunogens comprise a pathogen (e.g., an inactivated pathogen). In other embodiments, the one or more immunogens comprise a pathogen product (e.g., including, but not limited to, a protein, peptide, polypeptide, nucleic acid, polysaccharide, or membrane component derived from the pathogen). In some embodiments, the one or more immunogens and the emulsion are combined in a single vessel.

In some embodiments, the present invention provides a method of inducing an immune response to a plurality of immunogens (e.g., protective antigen (PA) of Bacillus anthracis, rLcrV or LcrV10 protein of Yersinia pestis, and rHCR/A1 of Clostridium botulinum) in a subject comprising providing a composition comprising a nanoemulsion and the plurality of immunogens (e.g., pathogens inactivated by a nanoemulsion of the present invention, and/or one or a plurality of protein and/or peptide antigens derived from one or a plurality of pathogens (e.g., recombinantly produced)); and administering the composition to the subject under conditions such that the subject generates an immune response to the plurality of immunogens. The present invention is not limited by the plurality of immunogens utilized. For example, in some embodiments, the plurality of immunogens are pathogens inactivated by a nanoemulsion of the present invention or are isolated, purified and/or recombinant protein or peptide antigens, or derivatives or variants thereof, derived from the plurality of pathogens (e.g., vaccinia virus inactivated by a nanoemulsion, and/or protein antigens (e.g., including, but not limited to, protective antigen (PA), lethal factor (LF), edema factor (EF), and PA degradation products from B anthracis or gp160, gp120, gp41, Tat or Nef from HIV). For example, in some embodiments, the present invention provides a composition comprising a nanoemulsion (e.g., $W_{80}5EC$) and recombinant protective antigen of B. anthracis, recombinant rHCR/A1 of C. botulinum, and recombinant rLcrV (e.g., rLcrV10) protein of Y. pestis, and methods of using and/or administrating (e.g., nasally administrating) the composition to induce immune responses (e.g., immune responses specific to each of the immunogens) in a subject (e.g., thereby providing protective immunity to the subject from B. anthracis, C. botulinum, and/or Y. pestis. In some embodiments, immune responses in the subject comprise generation of antibodies to the immunogens. In some embodiments, the antibodies generated comprise IgG and/or IgA antibodies. In some embodiments, the immune responses generated in a subject via administration of a nanoemulsion composition comprising a plurality of immunogens (e.g., two, three, four, five, six, seven, eight, or more immunogens) are similar to (e.g., not detectably different than) immune responses that are generated in a subject via administration of a plurality of nanoemulsion compositions, wherein each nanoemulsion composition comprises a single immunogen (e.g., the antigen specific antibody titer levels in a subject administered a composition comprising plurality of immunogens is similar to the antigen specific antibody titer levels in a subject administered a plurality of nanoemulsion compositions wherein each composition comprises a single immunogen).

In some preferred embodiments, an immunogenic composition (e.g., vaccine) comprising a plurality of immunogens does not comprise a preservative. For example, in some preferred embodiments, an immunogenic composition (e.g., vaccine) comprising a plurality of immunogens does not comprise a mercury based preservative (e.g., thiomersal). In some embodiments, a composition comprising a nanoemulsion and a plurality of immunogens of the invention is utilized for the treatment and/or prophylaxis of infection or disease caused by a plurality of pathogens, especially treatment or prophylaxis, for example, of anthrax, plague and/or toxin poisoning. In some embodiments, an immunogenic composition comprising a nanoemulsion and plurality of immunogens comprises a nanoemulsion that skews the immune response toward a Th1 type immune response. The present invention is not limited by the type of nanoemulsion utilized. Indeed, a variety of nanoemulsions can be utilized including but not limited to $W_{80}5EC$, although the present invention is not so limited. For example, in some embodiments, the nanoemulsion is selected from one of the nanoemulsion formulations described herein. In some embodiments, the composition comprises between 0.5-50% nanoemulsion solution, although greater and lesser amounts also find use in the invention. For example, in some embodiments, the immunogenic composition comprises about 0.1%-0.5%, 0.5%-1.0%, 1.0%-10%, about 10%-20%, about 20%-30%, about 30%-40%, about 40%-50%, about 50%-60% or more nanoemulsion solution. In some embodiments, the immunogenic composition comprises 20% nanoemulsion solution (e.g., 20% $W_{80}5EC$ or other emulsion described herein). In some embodiments, the immunogenic composition comprises about 10% nanoemulsion solution. In some embodiments, the immunogenic composition comprises about 15% nanoemulsion solution. In some embodiments, the immunogenic composition comprises about 20% nanoemulsion solution. In some embodiments, the immunogenic composition comprises about 12% nanoemulsion solution. In some embodiments, the immunogenic composition comprises about 8% nanoemulsion solution. In some embodiments, the immunogenic composition comprises about 5% nanoemulsion solution. In some embodiments, the immunogenic composition comprises about 2% nanoemulsion solution. In some embodiments, the immunogenic composition comprises about 1% nanoemulsion solution. In some embodiments, an immunogenic composition (e.g., that is administered to a subject in order to generate an immune response in the subject) comprises between about 5 and 75 μg of each of the plurality of immunogens (e.g., between 5 and 75 μg of recombinant protective antigen (PA) of B. anthracis, between 5 and 75 μg of recombinant LcrV or LcrV10 of Y. pestis, and between 5 and 75 μg of recombinant receptor binding domain HCR/A1 of C. botulinum neurotoxin). In some embodiments, an immunogenic composition (e.g., that is administered to a subject in order to generate an immune response in the subject) comprises 20 μg of each of the plurality of immunogens (e.g., recombinant protective antigen (PA) of B. anthracis, LcrV or LcrV 10 of Y. pestis, and recombinant receptor binding domain HCR/A1 of C. botulinum neurotoxin). However, the present invention is not limited to this amount of immunogen. Indeed, a variety of doses of immunogen are contemplated to be useful in the present invention. For example, in some embodiments, it is expected that each dose (e.g., of an immunogenic composition comprising a plurality of immunogens (e.g., administered to a subject to induce an immune response (e.g., a protective immune response (e.g., protective immunity))) comprises 0.05-5000 μg of each immunogen (e.g., recombinant, isolated and/or purified immunogen (e.g., recombinant protective antigen (PA) of B. anthracis, LcrV or LcrV10 of Y. pestis, and/or recombinant receptor binding domain HCR/A1 of C. botulinum neurotoxin)). In some embodiments, each dose will comprise 1-500 μg, in some embodiments, each dose will comprise 350-750 μg, in some embodiments, each dose will comprise 50-200 μg, in some embodiments, each dose will comprise 10-100 μg of each immunogen, each dose will comprise 10-75 μg of each immunogen, each dose will comprise 25-75 μg of each immunogen, in some embodiments, each dose will comprise 10-25 μg, in some embodiments, each dose will comprise 20 μg of each immunogen (e.g., recombinant, isolated and/or purified immunogen (e.g., recombinant protective antigen (PA) of B. anthracis, LcrV or LcrV10 of Y. pestis, and/or recombinant receptor binding domain HCR/A1 of C. botulinum neurotoxin)). In some embodiments, each dose comprises an amount of the plurality of immunogens sufficient to generate an immune response. An effective amount of the plurality of immunogens in a dose need not be quantified, as long as the amount of immunogens generates an immune response in a subject when administered to the subject.

In some embodiments, the immunogenic composition is stable (e.g., at room temperature (e.g., for 12 hours, one day, two days, three days, four days, a week, two weeks, three weeks, a month, two months, three months, four months, five months, six months, 9 months, a year or more). In some embodiments, the immunogenic composition comprises a pharmaceutically acceptable carrier. The present invention is not limited to any particular pharmaceutically acceptable carrier. Indeed, any suitable carrier may be utilized including but not limited to those described herein. In some embodiments, the immunogenic composition further comprises an adjuvant. The present invention is not limited to any particular adjuvant and any one or more adjuvants described herein find use in a composition of the invention including but not limited to adjuvants that skew toward a Th1 immune response (e.g., that induces expression and/or activity of Th1 type cytokines (e.g., IFN-γ, TNF-α, IL2 and/or IL-12). In some embodiments, the immunogenic composition comprising a nanoemulsion and a plurality of immunogens comprises an adjuvant that skews the immune response toward a Th1 type immune response. In some embodiments, the immunogenic composition comprising a nanoemulsion and a plurality of immunogens does not comprise an adjuvant that skews the immune response toward a Th1 type immune response (e.g., the immunogenic composition comprising nanoemulsion and plurality of immunogens skews toward a Th1 immune response due to the nanoemulsion utilized and not the presence of an adjuvant). In some embodiments, the level of Th1-type cytokines increases to a greater extent than the level of Th2-type cytokines (e.g., cytokines levels are readily assessed using standard assays, See, e.g., Mosmann and Coffman, Ann. Rev. Immunol. 7:145-173, 1989). In some embodiments, the plurality of immunogens comprise pathogen products (e.g., including, but not limited to, a protein, peptide, polypeptide, nucleic acid, polysaccharide, or a membrane component derived from the pathogen). In some embodiments, the plurality of immunogens and the nanoemulsion are combined in a single vessel.

In some embodiments, the present invention provides a method of inducing an immune response to a plurality of immunogens (e.g., protective antigen (PA) of B. anthracis, LcrV or LcrV10 of Y. pestis, and/or receptor binding domain HCR/A1 of C. botulinum neurotoxin) in a subject comprising: providing an immunogenic composition comprising a nanoemulsion and protective antigen (PA) of B. anthracis, LcrV or LcrV10 of Y. pestis, and/or receptor binding domain HCR/A1 of C. botulinum neurotoxin, and administering the composition to the subject under conditions such that the subject generates an immune response toward protective antigen (PA) of B. anthracis, LcrV or LcrV10 of Y. pestis, and/or receptor binding domain HCR/A1 of C. botulinum neurotoxin. The present invention is not limited by the route chosen for administration of a composition of the present invention. In some embodiments, administering the immunogenic composition comprises contacting a mucosal surface of the subject with the composition. In a preferred embodiment, the mucosal surface comprises nasal mucosa. In some embodiments, the immune response comprises a systemic IgG response to the immunogens. In some embodiments, the immune response comprises a mucosal IgA response to the immunogens. In some embodiments, inducing an immune response induces immunity to B. anthracis, Y. pestis, and/or C. botulinum neurotoxin in the subject. In some embodiments, the immunity comprises systemic immunity. In some embodiments, the immunity comprises mucosal immunity. In some embodiments, a subject administered an immunogenic composition comprising a nanoemulsion and plurality of immunogens generates a Th1 type immune response. In some embodiments, the Th1 type immune response comprises enhanced expression of IFN-γ and/or TNF-α. In some embodiments, the level of Th1-type cytokines increases to a greater extent than the level of Th2-type cytokines. For example, in some embodiments, a subject administered an immunogenic composition comprising a nanoemulsion and plurality of immunogens induces a greater than 3 fold, greater than 5 fold, greater than 10 fold, greater than 20 fold, greater than 25 fold, greater than 30 fold or more enhanced expression of Th1 type cytokines, with lower increases (e.g., less than 3 fold, less than two fold or less) enhanced expression of Th2 type cytokines (e.g., IL-4, IL-5, and/or IL-10). In some embodiments, administration of an immunogenic composition comprising a nanoemulsion and a plurality of immunogens to a subject generates immunogen specific antibodies in the subject. In some embodiments, the immunogen specific antibodies have a prevalence of IgG2b and/or IgG2a antibodies over that of IgG1 antibodies. In some embodiments, administration of an immunogenic composition comprising a nanoemulsion and a HBV immunogen to a subject generates immunogen specific IgA antibodies in the subject. The present invention is not limited to any particular nanoemulsion utilized in a method of inducing an immune response to a plurality of immunogens in a subject. Indeed, a variety of nanoemulsions may be utilized including but not limited to $W_{80}5EC$. For example, in some embodiments, the nanoemulsion is selected from one of the nanoemulsion formulations described herein. In a preferred embodiment, the immunogenic composition comprising a nanoemulsion and plurality of immunogens does not comprise an adjuvant that skews the immune response toward a Th1 type immune response (e.g., the immunogenic composition comprising nanoemulsion and plurality of immunogens skews toward a Th1 immune response due to the nanoemulsion utilized and not the presence of an adjuvant). In some embodiments, each dose comprises an amount nanoemulsion and plurality of immunogens sufficient to generate an immune response to the plurality of immunogens in a subject. An effective amount of nanoemulsion and plurality of immunogens is a dose that need not be quantified, as long as the amount nanoemulsion and plurality of immunogens generates immunogen-specific immune responses in a subject when administered to the subject. In some embodiments, each dose will comprise 1-500 μg, in some embodiments, each dose will comprise 350-750 μg, in some embodiments, each dose will comprise 50-200 μg, in some embodiments, each dose will comprise 10-100 μg of each immunogen, each dose will comprise 10-75 μg of each immunogen, each dose will comprise 25-75 μg of each immunogen, in some embodiments, each dose will comprise 10-25 μg, in some embodiments, each dose will comprise 20 μg of each immunogen (e.g., recombinant, isolated and/or purified immunogen (e.g., recombinant protective antigen (PA) of *B. anthracis*, LcrV or LcrV10 of *Y. pestis*, and/or recombinant receptor binding domain HCR/A1 of *C. botulinum* neurotoxin)). In some embodiments, a 20% nanoemulsion solution is utilized. In some embodiments, the nanoemulsion comprises $W_{80}5EC$. In some embodiments, the immunity protects the subject from displaying signs or symptoms of disease caused by the immunogens. In some embodiments, the immunity protects the subject from challenge with a subsequent exposure to live pathogens from which the immunogens are derived (e.g., *B. anthracis*, *Y. pestis*, and/or *C. botulinum* neurotoxin). In some embodiments, the immunogenic composition further comprises an adjuvant. In some embodiments, the subject is a human.

The present invention is not limited to any specific nanoemulsion composition. Indeed, a variety of nanoemulsion compositions are described herein that find use in the present invention. Similarly, the present invention is not limited to a particular oil present in the nanoemulsion. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent. Nanoemulsion components including oils, solvents and others are described in further detail below.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In some embodiments, the present invention provides a vaccine comprising an immunogenic composition comprising a nanoemulsion and plurality of immunogens. In some embodiments, the invention provides a kit comprising a vaccine, the vaccine comprising an immunogenic composition comprising a nanoemulsion and plurality of immunogens, the nanoemulsion comprising an aqueous phase, an oil phase, and a solvent. In some embodiments, the kit further comprises instructions for using the kit for vaccinating a subject against a plurality of immunogens (e.g., *B. anthracis*, *Y. pestis*, and/or *C. botulinum* neurotoxin).

In still further embodiments, the present invention provides a method of inducing immunity to a plurality of immunogens (*B. anthracis*, *Y. pestis*, and/or *C. botulinum* neurotoxin), comprising providing an emulsion comprising an aqueous phase, an oil phase, and a solvent; and a plurality of immunogens; combining the emulsion with the plurality of immunogens to generate a vaccine composition; and administering the vaccine composition to a subject. In some embodiments, administering comprises contacting the vaccine composition with a mucosal surface of the subject. For example, in some embodiments, administering comprises intranasal administration. In some preferred embodiments, the administering occurs under conditions such that the subject generates immunity to a plurality of pathogens (e.g., *B. anthracis*, *Y. pestis*, and/or *C. botulinum* neurotoxin (e.g., via generating humoral immune responses to the one or more immunogens)).

The present invention is not limited by the nature of the immune response generated (e.g., post administration of an immunogenic composition comprising a nanoemulsion and plurality of immunogens). Indeed, a variety of immune responses may be generated and measured in a subject administered a composition comprising an immunogenic composition comprising a nanoemulsion and plurality of immunogens of the present invention including, but not limited to, activation, proliferation or differentiation of cells of the immune system (e.g., B cells, T cells, dendritic cells, antigen presenting cells (APCs), macrophages, natural killer (NK) cells, etc.); up-regulated or down-regulated expression of markers and cytokines; stimulation of IgA, IgM, and/or IgG titers; splenomegaly (e.g., increased spleen cellularity); hyperplasia, mixed cellular infiltrates in various organs, and/or other responses (e.g., of cells) of the immune system that can be assessed with respect to immune stimulation known in the art. In some embodiments, administering comprises contacting a mucosal surface of the subject with the composition. The present invention is not limited by the mucosal surface contacted. In some preferred embodiments, the mucosal surface comprises nasal mucosa. In some embodiments, the mucosal surface comprises vaginal mucosa. In some embodiments, administering comprises parenteral administration. The present invention is not limited by the route chosen for administration of a composition of the present invention. In some embodiments, inducing an immune response induces immunity to a plurality of immunogens in the subject. In some embodiments, the immunity comprises systemic immunity. In some embodiments, the immunity comprises mucosal immunity. In some embodiments, the immune response comprises increased expression of IFN-γ and/or TNF-α in the subject. In some embodiments, the immune response comprises a systemic IgG (e.g., IgG2b and/or IgG2a) response. In some embodiments, the immune response comprises a mucosal IgA response. In some embodiments, the composition comprises a 20% nanoemulsion solution. However, the present invention is not limited to this amount (e.g., percentage) of nanoemusion. For example, in some embodiments, an immunogenic composition comprises less than 20% nanoemulsion (e.g., 19%, 18%, 17%, 16%, 15%, 14%, 13%, 12%, 11%, 10%, 9%, 8%, 7%, 6%, 5%, 4%, 3%, 2%, 1% or less nanoemulsion). In some embodiments, an immunogenic composition comprises more than 20% nanoemulsion (e.g., 25%, 30%, 35%, 40%. 45%, 50%, 60% or more). In some embodiments, an immunogenic composition of the present invention comprises any of the nanoemulsions described herein. In some embodiments, the nanoemulsion comprises $W_{20}5EC$. In some preferred embodiments, the nanoemulsion comprises $W_{80}5EC$. In some embodiments, the nanoemulsion is X8P. In some embodiments, immunity protects the subject from displaying signs or symptoms of disease caused by a plurality of pathogens (e.g., *B. anthracis, Y. pestis,* and/or *C. botulinum* neurotoxin). In some embodiments, an immunogenic composition further comprises an adjuvant. The present invention is not limited by the type of adjuvant utilized. In some embodiments, the adjuvant is a CpG oligonucleotide. In some embodiments, the adjuvant is monophosphoryl lipid A. A number of other adjuvants that find use in the present invention are described herein. In some embodiments, the subject is a human. In some embodiments, the immunity protects the subject from displaying signs or symptoms of a infection with or exposure to a plurality of pathogens (e.g., *B. anthracis, Y. pestis,* and/or *C. botulinum* neurotoxin). In some embodiments, immunity reduces the risk of infection, disease and/or morbidity upon one or more exposures to a plurality of pathogens (e.g., *B. anthracis, Y. pestis,* and/or *C. botulinum* neurotoxin).

DESCRIPTION OF THE FIGURES

The following figures form part of the present specification and are included to further demonstrate certain aspects and embodiments of the present invention. The invention may be better understood by reference to one or more of these figures in combination with the description of specific embodiments presented herein.

The following figures form part of the present specification and are included to further demonstrate certain aspects and embodiments of the present invention. The invention may be better understood by reference to one or more of these figures in combination with the description of specific embodiments presented herein.

FIG. 1 shows PAGE analysis of recombinant antigens. Protein samples loaded at 0.5 ug/well. Antigens appear intact and do not contain contaminants.

FIG. 2 shows the immunogenicity of trivalent NE-based nasal vaccines composed of HCR/A1, PA and either LcrV10 shown in (A) or LcrV shown in (B) mixed with nanoemulsion.

Figure 3:
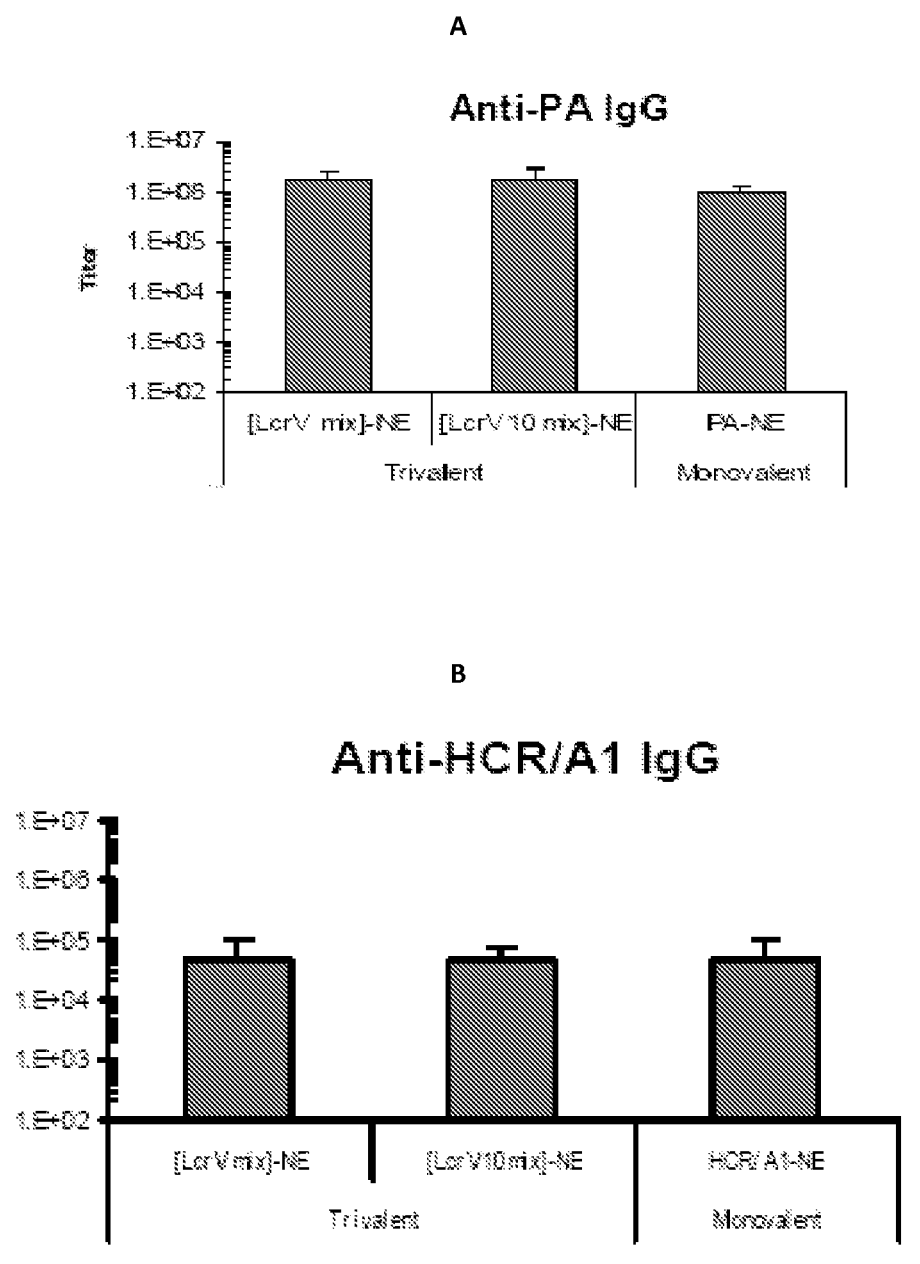
Figure 3:
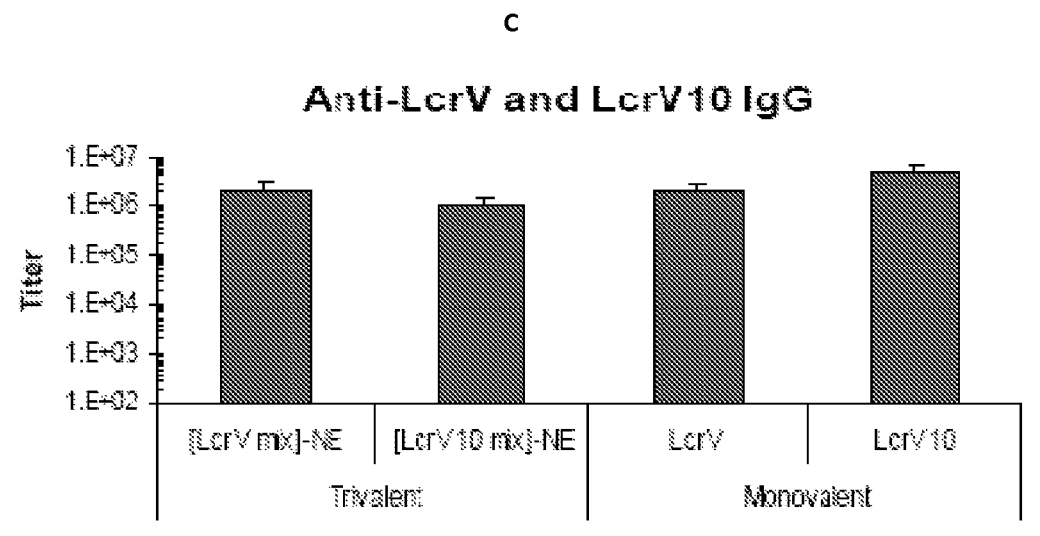

FIG. 3 shows a comparison of the immunogenicity if trivalent (HCR/A1-LcrV-PA)-NE vaccines versus monovalent NE-based vaccines for PA shown in (A), HCR/A1 shown in (B), and LcrV and LcrV10 shown in (C).

FIG. 8 shows the Th-1 type anti-LcrV and Lcrv10 IgG subclass pattern in mice immunized with the trivalent mucosal vaccine.

FIG. 10 shows protective immunity generated in a subject administered an intranasal trivalent vaccine of the invention against challenge with live *Yersinia pestis* strain C092.

FIG. 11 shows protective immunity generated in a subject administered an intranasal trivalent vaccine of the invention against challenge with live *Yersinia pestis* strain C092.

GENERAL DESCRIPTION OF THE INVENTION

Figure 4:
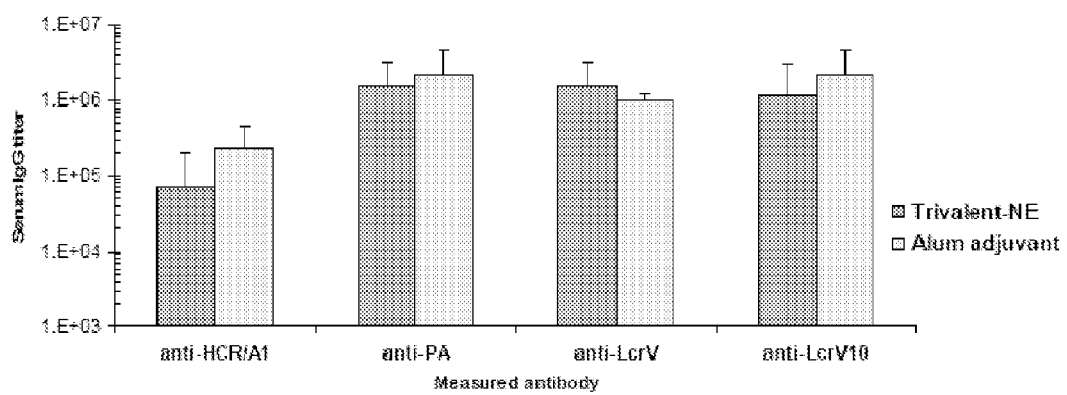
FIG. 4 shows that immunogenicity of nasal NE-adjuvanted trivalent vaccine was compared to that of intramuscular injected alum-based vaccine.

The present invention provides methods and compositions for the stimulation of immune responses. Specifically, the present invention provides methods of inducing an immune response against one or a plurality of pathogens (e.g., vaccinia virus, H5N1 influenza virus, *Bacillus anthracis, C. botulinum, Y. pestis,* Hepatitis B, and/or HIV, etc.) in a subject (e.g., a human subject) and compositions useful in such methods (e.g., a nanoemulsion comprising one or a plurality of pathogens (e.g., inactivated by the nanoemulsion) and/or pathogen products and/or pathogen components). Compositions and methods of the present invention find use in, among other things, clinical (e.g. therapeutic and preventative medicine (e.g., vaccination)) and research applications. In some embodiments, one or a plurality of pathogens are mixed with a nanoemulsion prior to administration for a time period sufficient to inactivate the one or plurality of pathogens. In some embodiments, one or a plurality of protein components (e.g., isolated and/or purified and/or recombinant protein) from one or a plurality of pathogens are mixed with the nanoemulsion.

Although an understanding of the mechanism is not necessary to practice the present invention and the present invention is not limited to any particular mechanism of action, in some embodiments, NE treatment (e.g., neutralization of one or more pathogens) with a NE of the present invention preserves important antigenic epitopes (e.g., recognizable by a subject's immune system), stabilizing their hydrophobic and hydrophilic components in the oil and water interface of the emulsion (e.g., thereby providing one or more immunogens (e.g., stabilized antigens) against which a subject can mount an immune response). In other embodiments, because NE formulations penetrate the mucosa through pores, they may carry immunogens to the submucosal location of dendritic cells (e.g., thereby initiating and/or stimulating an immune response). Although an understanding of the mechanism is not necessary to practice the present invention and the present invention is not limited to any particular mechanism of action, in some embodiments, combining a NE and one or a plurality of immunogenic proteins (e.g., rPA from *B. anthracis*, rHCR/A1 (fragment of *C. botulinum* neurotoxin), rLcrV (or LcrV10) protein of *Y. pestis* and/or gp120 from HIV, etc.) stabilizes the immunogens and provides a proper immunogenic material for generation of an immune response.

Furthermore, in some embodiments, a composition of the present invention (e.g., a composition comprising a NE and one or a plurality of immunogens) induces (e.g., when administered to a subject) both systemic and mucosal immunity. Thus, in some preferred embodiments, administration of a composition of the present invention to a subject results in protection against an exposure (e.g., a lethal mucosal exposure) to one or a plurality of pathogens (e.g., one or a plurality of viruses and/or bacteria). Although an understanding of the mechanism is not necessary to practice the present invention and the present invention is not limited to any particular mechanism of action, mucosal administration (e.g., vaccination) provides protection against pathogen infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3ed edn. (Academic Press, San Diego, 2005)), the present invention provides compositions and methods for stimulating mucosal immunity (e.g., a protective IgA response) against one or a plurality of pathogens in a subject.

In some embodiments, the present invention provides a composition (e.g., comprising a NE and one or a plurality of immunogens) to serve as a mucosal vaccine. This material can easily be produced from purified virus and/or protein or recombinant protein and induces both mucosal and systemic immunity. The ability to produce this formulation rapidly and administer it via mucosal instillation provides vaccines that can be used for general vaccination needs as well as in large-scale outbreaks or emergent situations.

DEFINITIONS

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

As used herein, the terms "inactivating," "inactivation" and grammatical equivalents, when used in reference to a microorganism (e.g., a pathogen (e.g., a bacterium or a virus)), refer to the killing, elimination, neutralization and/or reducing of the capacity of the mircroorganism (e.g., a pathogen (e.g., a bacterium or a virus)) to infect and/or cause a pathological response and/or disease in a host. For example, in some embodiments, the present invention provides a composition comprising nanoemulsion (NE)-inactivated vaccinia virus (VV). Accordingly, as referred to herein, compositions comprising "NE-inactivated VV," "NE-killed V," NE-neutralized V" or grammatical equivalents refer to compositions that, when administered to a subject, are characterized by the absence of, or significantly reduced presence of, VV replication (e.g., over a period of time (e.g., over a period of days, weeks, months, or longer)) within the host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsions comprise an oil phase having droplets with a mean particle size of approximately 0.1 to 5 microns (e.g., 150+/−25 nm in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis(oxyethylenenitrilo)tetraacetic acid (EGTA), and the like) and certain biological agents (e.g., bovine serum abulmin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises a nanoemulsion and an immunogen. In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion and an immunogen is administered to a subject as a vaccine (e.g., to prevent or attenuate a disease (e.g., by providing to the subject total or partial immunity against the disease or the total or partial attenuation (e.g., suppression) of a sign, symptom or condition of the disease.

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, saponins purified from the bark of the Q. *saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present invention (e.g., comprising HIV or an immunogenic epitope thereof (e.g., gp120)) are administered with one or more adjuvants (e.g., to skew the immune response towards a Th1 or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen (e.g., gp120 or rPA))) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application of a composition of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, formix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION OF THE INVENTION

The present invention provides methods and compositions for the stimulation of immune responses. Specifically, the present invention provides methods of inducing an immune response against one or a plurality of pathogens (e.g., vaccinia virus, H5N1 influenza virus, *Bacillus anthracis, C. botulinum, Y. pestis*, Hepatitis B, and/or HIV, etc.) in a subject (e.g., a human subject) and compositions useful in such methods (e.g., a nanoemulsion comprising one or a plurality of pathogens (e.g., inactivated by the nanoemulsion) and/or pathogen products and/or pathogen components). Compositions and methods of the present invention find use in, among other things, clinical (e.g. therapeutic and preventative medicine (e.g., vaccination)) and research applications. In some embodiments, one or a plurality of pathogens are mixed with a nanoemulsion prior to administration for a time period sufficient to inactivate the one or plurality of pathogens. In some embodiments, one or a plurality of protein components (e.g., isolated and/or purified and/or recombinant protein) from one or a plurality of pathogens are mixed with the nanoemulsion.

Nanoemulsion Vaccine Compositions and Compositions for Inducing Immune Responses In some embodiments, the present invention provides compositions for inducing immune responses comprising a nanoemulsion and one or more immunogens (e.g., inactivated pathogens or pathogen products). The present invention provides immunogenic compositions capable of generating an immune response against any number of pathogens (e.g., vaccines for any number of pathogens). A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes).

Immunogens (e.g., pathogens or pathogen products) and nanoemulsions of the present invention may be combined in any suitable amount utilizing a variety of delivery methods. Any suitable pharmaceutical formulation may be utilized, including, but not limited to, those disclosed herein. Suitable formulations may be tested for immunogenicity using any suitable method. For example, in some embodiments, immunogenicity is investigated by quantitating both antibody titer and specific T-cell responses. Nanoemulsion compositions of the present invention may also be tested in animal models of infectious disease states. Suitable animal models, pathogens, and assays for immunogenicity include, but are not limited to, those described below.

In some preferred embodiments, the present invention provides methods of inducing an immune response to a plurality of pathogenic organisms in a subject (e.g., a human subject) and compositions useful in such methods (e.g., a nanoemulsion composition comprising a plurality of pathogens and/or plurality of pathogen components (e.g., a plurality of isolated and/or recombinant pathogenic proteins (e.g., protective antigen (PA) of *B. anthracis*, recombinant rHCR/A1 of *C. botulinum*, and recombinant rLcrV (e.g., rLcrV10) protein of *Y. pestis* (e.g., as described in Examples 1 and 2). In some embodiments, methods of inducing an immune response to a plurality of pathogens provided by the present invention are used for vaccination. For example, in some embodiments, the present invention provides a composition comprising a nanoemulsion and one or a plurality of immunogens (e.g., derived from a plurality of pathogens (e.g., one or a plurality of pathogens inactivated by a nanoemulsion of the present invention and/or one or a plurality of protein and/or peptide antigens derived from (e.g., isolated and/or recombinantly produced from) one or a plurality of pathogens); as well as methods of administering the composition (e.g., nasally administering) to a subject under conditions such that the subject generates an immune response to the one or a plurality of pathogens and/or immunogens. In some embodiments, administrating comprises mucosal administration. In some embodiments, inducing an immune response induces immunity to each of the plurality of immunogens in the subject. In some embodiments, inducing an immune response to the immunogens induces immunity to the plurality of pathogens from which the immunogens are derived. In some embodiments, immunity comprises systemic immunity. In some embodiments, immunity comprises mucosal immunity. In some embodiments, the immune response comprises increased expression of IFN-γ in the subject. In some embodiments, the immune response comprises a systemic IgG response to the immunogens (e.g., comparable to monovalent vaccine formulations). In some embodiments, the immune response comprises a mucosal IgA response to the immunogens. In some embodiments, the immune response to a multivalent immunogenic composition is characterized by a balanced Th1/Th2 polarization (e.g., an IgG subclass distribution and cytokine response indicative of a balanced Th1/Th2 response). Thus, the present invention provides that a multivalent immunogenic composition comprising a nanoemulsion and a plurality of immunogens provides an environment for the plurality of immunogens that maintains the conformation and/or presence of immunogenic epitopes important for protective immunity (e.g., that are recognized by and acted upon by a hosts immune system (e.g., humoral and/or cellular immune response)). In some embodiments, a plurality of immunogens are combined (e.g., in any ratio) to optimize protection against a plurality of environmental pathogens from which the immunogens are derived. For example, in some embodiments, the present invention provides an immunogenic composition that is utilized as a combined anthrax, plague, and botulism vaccine. The present invention also provides that a multivalent immunogenic composition utilized as a vaccine produces immune responses in subjects that are comparable to standard alum-based vaccines. The present invention also provides that a multivalent, nanoemulsion immunogenic composition utilized as a vaccine provides protective immunity to a subject against lethal infection with a pathogenic organisms from which the nanoemulsion immunogenic composition is derived (e.g., plague and/or anthrax). The present invention is not limited to any particular pathogen, combination of pathogens, and/or combination of pathogen components (e.g., peptides, proteins, etc. (e.g., utilized in an immunogenic nanoemulsion composition (e.g., utilized to induce immune responses (e.g., protective immunity) to the pathogen components and/or pathogens))). In some embodiments, the present invention provides a method of inducing an immune response to a plurality of immunogens (e.g., protective antigen (PA) of *B. anthracis*, LcrV or LcrV10 of *Y. pestis*, and/or receptor binding domain HCR/A1 of *C. botulinum* neurotoxin) in a subject comprising: providing an immunogenic composition comprising a nanoemulsion and protective antigen (PA) of *B. anthracis*, LcrV or LcrV10 of *Y. pestis*, and/or receptor binding domain HCR/A1 of *C. botulinum* neurotoxin, and administering the composition to the subject under conditions such that the subject generates an immune response toward protective antigen (PA) of *B. anthracis, LcrV or LcrV*10 of *Y. pestis*, and/or receptor binding domain HCR/A1 of *C. botulinum* neurotoxin.

Experiments conducted during development of embodiments of the invention documented the immunogenicity of a novel, mucosal multivalent vaccine that is based on a mixture of recombinant antigens (e.g., protective antigen (PA) of *B. anthracis*, LcrV or LcrV10 of *Y. pestis*, and/or receptor binding domain HCR/A1 of *C. botulinum* neurotoxin) and nanoemulsion adjuvant. A single nasal immunization multivalent nanoemulsion mixture produced a rapid induction of serum anti-immunogen IgGs, which was comparable to that achieved with intramuscular (i.m.) vaccination using aluminum salt-based vaccine (See Examples 1 and 2). Mucosal NE-adjuvanted vaccines produced rapid, robust and sustainable serum IgG and mucosal responses to all three antigens. Bronchoalveolar lavages (BAL) and serum were analyzed for IgG and IgA. BAL and serum IgA levels indicated presence of mucosal immunity. Comparison of immunogenicity of trivalent vs. monovalent NE-based formulations indicated that combining PA, HCR/A1 and LcrV (or V10) did not affect the immunogenicity of individual antigen. Nasal NE-adjuvanted vaccines elicited serum IgG responses comparable with intramuscular injection of alum-based vaccines. Challenge studies with spores of Ames strain of anthrax spores and with a virulent *Y. pestis* C092 indicate that nasal immunizations with NE-based vaccines produced protective immunity against anthrax and plague in rodent models (See Examples 1-2). Thus, in some embodiments, the present invention provides a multivalent nanoemulsion vaccine (e.g., against anthrax, plague and botulinum toxin). Thus, the present invention provides that vaccination (e.g., intranasal administration) with a multivalent vaccine obviates the need for injection or an inflammatory adjuvant. The present invention also provides a straight forward approach for formulation of an immunogenic composition (e.g., for use as a multivalent vaccine) that makes it suitable to be produced without special equipment. Thus, in some embodiments, compositions described herein are utilized in developing regions of the world. The present invention significantly decreases costs associated with conventional multivalent vaccines (e.g., the need to maintain conventional vaccines at a refrigerated temperature is overcome by the present invention). Since the multivalent vaccine retained immunogenicity after storage, in some embodiments, the vaccine does not require refrigeration during distribution.

Adjuvants have been traditionally developed from pro-inflammatory substances, such as a toxin or microbiological component, found to trigger signaling pathways and cytokine production (See, e.g., Graham, B. S., Plos Medicine, 2006. 3(1): p. e57). Also, enterotoxin-based adjuvants, such as cholera toxin, have been associated with inducing inflammation in the nasal mucosa and with production of the inflammatory cytokines and transport of the vaccine along olfactory neurons into the olfactory bulbs (See, e.g., van Ginkel, F. W., et al., Infect Immun., 2005. 73(10): p. 6892-6902). Some patients treated with a flu vaccine based on one of these toxins (NASALFLU, BERNA Biotech), developed Bell's palsy (See, e.g., Mutsch, M., et al., New England Journal of Medicine, 2004. 350(9): p. 896-903) presumably due to the vaccine in the olfactory bulb. This finding led to NASALFLU being withdrawn. The present invention provides a composition with no significant inflammation in HBsAg-NE treated animals and no evidence of the vaccine composition in the olfactory bulb. Thus the present invention provides, in some embodiments, compositions and methods for inducing immune responses (e.g., immunity to) to a plurality of pathogens utilizing needle-free mucosal administration, induction of systemic immunity comparable with conventional vaccines, as well as mucosal and cellular immune responses that are not elicited by injected, aluminum-based vaccines.

Pathogens

The present invention is not limited to the use of any one specific type of pathogen (e.g., for providing one or more immunogens (e.g., antigens) for use in a composition comprising a nanoemulsion and a plurality of immunogens. Indeed, compositions (e.g., comprising a NE and a plurality of immunogens) useful for generating an immune response (e.g., for use as a vaccine) to a variety of pathogens are within the scope of the present invention. Accordingly, in some embodiments, the present invention provides compositions for generating an immune response to bacterial pathogens (e.g., in vegetative or spore forms) including, but not limited to, *Bacillus cereus, Bacillus circulans* and *Bacillus megaterium, Bacillus anthracis*, bacteria of the genus *Brucella, Vibrio cholera, Coxiella burnetii, Francisella tularensis, Chlamydia psittaci, Ricinus communis, Rickettsia prowazekii*, bacterial of the genus *Salmonella* (e.g., *S. typhi*), bacteria of the genus *Shigella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia pestis, Yersinia enterocolitica*, and *Yersinia pseudotuberculosis*). In other embodiments, the present invention provides compositions for generating an immune response to viral pathogens including, but not limited to, influenza A virus, avian influenza virus, H5N1 influenza virus, West Nile virus, SARS virus, Marburg virus, Arenaviruses, Nipah virus, alphaviruses, filoviruses, herpes simplex virus I, herpes simplex virus II, sendai, sindbis, vaccinia, parvovirus, human immunodeficiency virus, hepatitis B virus, hepatitis C virus, hepatitis A virus, cytomegalovirus, human papilloma virus, picornavirus, hantavirus, junin virus, and ebola virus). In still further embodiments, the present invention provides compositions for generating an immune response to fungal pathogens, including, but not limited to, *Candida albicnas* and *parapsilosis, Aspergillus fumigatus* and *niger, Fusarium* spp, *Trychophyton* spp.

Bacteria for use in formulating a composition for generating an immune response of the present invention can be obtained from commercial sources, including, but not limited to, American Type Culture Collection (ATCC). In some embodiments, bacteria are passed in animals prior to being mixed with nanoemulsions in order to enhance their pathogenicity for each specific animal host for 5-10 passages (Sinai et al., J. Infect. Dis., 141:193 (1980)). In some embodiments, the bacteria then are then isolated from the host animals, expanded in culture and stored at −80° C. Just before use, the bacteria are thawed and grown on an appropriate solid bacterial culture medium overnight. The next day, the bacteria are collected from the agar plate and suspended in a suitable liquid solution (e.g., Brain Heart Infusion (BHI) broth). The concentration of bacteria is adjusted so that the bacteria count is approximately $1.5 \times 10^8$ colony forming units per ml (CFU/ml), based on the McFarland standard for bactericidal testing (Hendrichson and Krenz, 1991).

Viruses for use in formulating a composition for generating an immune response of the present invention can be obtained from commercial sources, including, but not limited to, ATCC. In some embodiments, viruses are passed in the prospective animal model for 5-10 times to enhance pathogenicity for each specific animal (Ginsberg and Johnson, Infect. Immun., 13:1221 (1976)). In some embodiments, the virus is collected and propagated in tissue culture and then purified using density gradient concentration and ultracentrifugation (Garlinghouse et al., Lab Anim Sci., 37:437 (1987); and Mahy, Br. Med. Bull., 41:50 (1985)). The Plaque Forming Units (PFU) are calculated in the appropriate tissue culture cells.

Lethal dose and/or infectious dose for each pathogen can be calculated using any suitable method, including, but not limited to, by administering different doses of the pathogens to the animals by the infective route and identifying the doses which result in the expected result of either animal sickness or death based on previous publications (Fortier et al., Infect Immun., 59:2922 (1991); Jacoby, Exp Gerontol., 29:89 (1994); and Salit et al., Can J. Microbiol., 30:1022 (1984)).

Generation of Antibodies

An immunogenic composition comprising a nanoemulsion and plurality of immunogens (e.g., protective antigen (PA) of B. anthracis, LcrV or LcrV10 of Y. pestis, and/or receptor binding domain HCR/A1 of C. botulinum neurotoxin) can be used to immunize a mammal, such as a mouse, rat, rabbit, guinea pig, monkey, or human, to produce antibodies (e.g., polyclonal antibodies). If desired, one or more of a plurality of immunogens (e.g., protective antigen (PA) of B. anthracis, LcrV or LcrV10 of Y. pestis, and/or receptor binding domain HCR/A1 of C. botulinum neurotoxin) can be conjugated to a carrier protein, such as bovine serum albumin, thyroglobulin, keyhole limpet hemocyanin or other carrier described herein, mixed with a nanoemulsion and administered to a subject. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, nanoemulsions described herein, keyhole limpet hemocyanin, and dinitrophenol). Among adjuvants used in humans, BCG (bacilli Calmette-Guerin) and Corynebacterium parvum are especially useful.

Monoclonal antibodies that specifically bind one or more of a plurality of immunogens (e.g., protective antigen (PA) of B. anthracis, LcrV or LcrV10 of Y. pestis, and/or receptor binding domain HCR/A1 of C. botulinum neurotoxin) can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984).

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies which specifically bind to a particular antigen also can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound.

The bound antibodies can then be eluted from the column using a buffer with a high salt concentration.

Nanoemulsions

The nanoemulsion vaccine compositions of the present invention are not limited to any particular nanoemulsion. Any number of suitable nanoemulsion compositions may be utilized in the vaccine compositions of the present invention, including, but not limited to, those disclosed in Hamouda et al., J. Infect Dis., 180:1939 (1999); Hamouda and Baker, J. Appl. Microbiol., 89:397 (2000); and Donovan et al., Antivir. Chem. Chemother., 11:41 (2000), as well as those shown in Tables 1 and 2. Preferred nanoemulsions of the present invention are those that are effective in killing or inactivating pathogens and that are non-toxic to animals. Accordingly, preferred emulsion formulations utilize non-toxic solvents, such as ethanol, and achieve more effective killing at lower concentrations of emulsion. In preferred embodiments, nanoemulsions utilized in the methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., on a battlefield). In some embodiments, one of the nanoemulsions described in Table 1 is utilized.

In some preferred embodiments, the emulsions comprise (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in the compositions of the present invention include but are not limited to one or more, organic, and more particularly, organic phosphate based solvents, surfactants and detergents, quaternary ammonium containing compounds, cationic halogen containing compounds, germination enhancers, interaction enhancers, and pharmaceutically acceptable compounds. Certain exemplary embodiments of the various compounds contemplated for use in the compositions of the present invention are presented below.

TABLE 1

Nanoemulsion Formulations

| Name | Oil Phase Formula | Water to Oil Phase Ratio (Vol/Vol) |
|---|---|---|
| X8P | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |

TABLE 1-continued

Nanoemulsion Formulations

| Name | Oil Phase Formula | Water to Oil Phase Ratio (Vol/Vol) |
|---|---|---|
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

TABLE 2

Nanoemulsion Formulations

| Nanoemulsion | Composition |
|---|---|
| X8P | 8% TRITON X-100; 8% Tributyl phosphate; 64% Soybean oil; 20% Water |
| $W_{20}5EC$ | 5% TWEEN 20; 8% Ethanol; 1% Cetylpyridinium Chloride; 64% Soybean oil; 22% Water |
| EC | 1% Cetylpyridinium Chloride; 8% Ethanol; 64% Soybean oil; 27% Water |
| Y3EC | 3% TYLOXAPOL; 1% Cetylpyridinium Chloride; 8% Ethanol; 64% Soybean oil; 24% Water |
| X4E | 4% TRITON X-100; 8% Ethanol; 64% Soybean oil; 24% Water |

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious against microbes and is also non-irritating and non-toxic to mammalian users (and can thus be contacted with mucosal membranes).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

The following description provides a number of exemplary emulsions including formulations for compositions X8P and $X_8W_{60}PC$. X8P comprises a water-in oil nanoemulsion, in which the oil phase was made from soybean oil, tri-n-butyl phosphate, and TRITON X-100 in 80% water. $X_8W_{60}PC$ comprises a mixture of equal volumes of X8P with $W_{80}8P$. $W_{80}8P$ is a liposome-like compound made of glycerol monostearate, refined soya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Emulsion formulations are given in Table 1 for certain embodiments of the present invention. These particular formulations may be found in U.S. Pat. No. 5,700,679 (NN); U.S. Pat. Nos. 5,618,840; 5,549,901 ($W_{80}{}^8P$); and U.S. Pat. No. 5,547,677, herein incorporated by reference in their entireties.

The $X8W_{60}PC$ emulsion is manufactured by first making the $W_{80}8P$ emulsion and X8P emulsions separately. A mixture of these two emulsions is then re-emulsified to produce a fresh emulsion composition termed $X8W_{60}PC$. Methods of producing such emulsions are described in U.S. Pat. Nos.

5,103,497 and 4,895,452 (herein incorporated by reference in their entireties). These compounds have broad-spectrum antimicrobial activity, and are able to inactivate vegetative bacteria through membrane disruption.

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising X8P have a water to oil ratio of 4:1, it is understood that the X8P may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri(N-butyl)phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

The nanoemulsions structure of the certain embodiments of the emulsions of the present invention may play a role in their biocidal activity as well as contributing to the non-toxicity of these emulsions. For example, the active component in X8P, TRITON-X100 shows less biocidal activity against virus at concentrations equivalent to 11% X8P. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. It should be noted that when all the components of X8P are combined in one composition but are not in a nanoemulsion structure, the mixture is not as effective as an antimicrobial as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, the inventive formulation comprise from about 3 to 8 vol. % of TYLOXAPOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., DiH$_2$O or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 4.0 to about 10.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of DiH$_2$O (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of DiH$_2$O (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of DiH$_2$O (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of DiH$_2$O (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of DiH$_2$O (designated herein as Y4EC). In still another embodiment the formulation comprises about 8% TYLOXAPOL, about 8% ethanol, about 1 vol. % of CPC, and about 64 vol. % of soybean oil, and about 19 vol. % of DiH$_2$O (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, the inventive formulations comprise about 8 vol. % of ethanol, and about 1 vol. % of CPC, and about 64 vol. % of oil (e.g., soybean oil), and about 27 vol. % of aqueous phase (e.g., DiH$_2$O or PBS) (designated herein as EC).

In the present invention, some embodiments comprise from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., DiH$_2$O or PBS) (designated herein as S8P).

In certain embodiments of the present invention, the inventive formulation comprise from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., DiH$_2$O or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase DiH$_2$O. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In a preferred embodiment of the present invention, the formulations comprise from about 5 vol. % of TWEEN 80, from about 8 vol. % of ethanol, from about 1 vol. % of CPC, about 64 vol. % of oil (e.g., soybean oil), and about 22 vol. % of DiH$_2$O (designated herein as W$_{80}$5EC).

In still other embodiments of the present invention, the formulations comprise from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In still other embodiments of the present invention, the formulations comprise from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., DiH$_2$O or PBS). For example, the present invention contemplates formulations comprising about 2 vol. % of TRITON X-100, about 8 vol. % of ethanol, about 64 vol. % of soybean oil, and about 26 vol. % of DiH$_2$O (designated herein as X2E). In other similar embodiments, the formulations comprise about 3 vol. % of TRITON X-100, about 8 vol. % of ethanol, about 64 vol. % of soybean oil, and about 25 vol. % of DiH$_2$O (designated herein as X3E). In still further embodiments, the formulations comprise about 4 vol. % TRITON X-100, about 8 vol. % of ethanol, about 64 vol. % of soybean oil, and about 24 vol. % of DiH$_2$O (designated herein as X4E). In yet other embodiments, the formulations comprise about 5 vol. % of TRITON X-100, about 8 vol. % of ethanol, about 64 vol. % of soybean oil, and about 23 vol. % of DiH$_2$O (designated herein as X5E). Another embodiment of the present invention comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, the formulations comprise about 8 vol. % of TRITON X-100, about 8 vol. % of ethanol, about 64 vol. % of soybean oil, and about 20 vol. % of DiH$_2$O (designated herein as X8E). In still further embodiments of the present invention, the formulations comprise about 8 vol. % of TRITON X-100, about 8 vol. % of ethanol, about 64 vol. % of olive oil, and about 20 vol. % of DiH$_2$O (designated herein as X8E 0). In yet another embodiment comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, the formulations comprise from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these formulations may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some of the embodiments comprising liquid baby formula, the formula comprises a casein hydrolysate (e.g., Neutramigen, or Progestimil, and the like). In some of these embodiments, the inventive formulations further comprise from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, the formulations comprise about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, the formulations comprise about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, the formulations comprise about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, the formulations comprise about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated herein as 90% X2Y2PC/YE).

In some embodiments of the present invention, the inventive formulations comprise about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, the inventive formulations comprise about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, the inventive formulations comprise from about 4 to 8 vol. % of TRITON X-100, from about 5 to 8 vol. % of TBP, about 30 to 70 vol. % of oil (e.g., soybean or olive oil), and 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethylety-lammonium bromide, 500 μM EDTA, about 10 mM ammonium chloride, about 5 mM Inosine, and about 5 mM L-alanine. For example, in certain of these embodiments, the inventive formulations comprise about 8 vol. % of TRITON X-100, about 8 vol. % of TBP, about 64 vol. % of soybean oil, and about 20 vol. % of DiH$_2$O (designated herein as X8P). In another embodiment of the present invention, the inventive formulations comprise about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, the formulations comprise about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). Another embodiment of the present invention comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). Still another related embodiment comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, the inventive formulations comprise about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, the inventive formulations comprise about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, the formulation comprise about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, the formulations comprise about 8 vol. % of TRITON X-100, about 8 vol. % of TBP, about 1 vol. % of cetyldimethylethylammonium bromide, about 50 vol. % of soybean oil, and about 33 vol. % of DiH$_2$O (designated herein as X8P CTAB). In still further embodiments, the present invention comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). Additional similar embodiments comprise 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, the inventive formulations further comprise about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, the inventive formulations comprise about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, the formulations comprise about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain related embodiments further comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, the inventive formulations comprise about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, the inventive formulations comprise about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment the formulations comprise about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). Another related embodiment comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, the inventive formulations comprise from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, the present invention comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, the formulations comprise about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, the inventive formulations comprise about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, one embodiment of the present invention comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, the inventive formulations comprise about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, the inventive formulations comprise about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of L-ascorbic acid. For example, one particular embodiment comprises about 8 vol. % of glycerol, about 1 vol. % of CPC, about 64 vol. % of soybean oil, and about 27 vol. % of DiH$_2$O (designated herein as GC). An additional related embodiment comprises about 10 vol. % of glycerol, about 10 vol. % of CPC, about 60 vol. % of soybean oil, and about 20 vol. % of DiH$_2$O (designated herein as GC10). In still another embodiment of the present invention, the inventive formulations comprise about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$.

In some embodiments of the present invention, the inventive formulations comprise about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, the inventive formulations comprise about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, the inventive formulations comprise about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, the inventive formulations comprise about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of compositions that find use in the present invention. The present invention contemplates that many variations of the above formulation, as well as additional nanoemulsions, find use in the methods of the present invention. To determine if a candidate emulsion is suitable for use with the present invention, three criteria may be analyzed. Using the methods and standards described herein, candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O did not form an emulsion.

Second, in preferred embodiments, the candidate emulsion should form a stable emulsion. An emulsion is stable if it remains in emulsion form for a sufficient period to allow its intended use. For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O did not form a stable emulsion. The following candidate emulsions were shown to be stable using the methods described herein: 0.08% TRITON X-100, 0.08% Glycerol, 0.01% Cetylpyridinium Chloride, 99% Butter, and 0.83% diH$_2$O (designated herein as 1% X8GC Butter); 0.8% TRITON X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% NATROSOL 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil).

Third, the candidate emulsion should have efficacy for its intended use. For example, an anti-bacterial emulsion should kill or disable pathogens to a detectable level. As shown herein, certain emulsions of the present invention have efficacy against specific microorganisms, but not against others. Using the methods described herein, one is capable of determining the suitability of a particular candidate emulsion against the desired microorganism. Generally, this involves exposing the microorganism to the emulsion for one or more time periods in a side-by-side experiment with the appropriate control samples (e.g., a negative control such as water) and determining if, and to what degree, the emulsion kills or disables the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% NATROSOL 250H NF, and 96% diH$_2$O (designated herein as 2% W$_{20}$5EC NATROSOL 2, also called 2% W$_{20}$5EC GEL); 2% W$_{20}$5EC, 1% NATROSOL 250H NF, and 97% diH$_2$O (designated herein as 2% W$_{20}$5EC NATROSOL 1); 2% W$_{20}$5EC, 3% NATROSOL 250H NF, and 95% diH$_2$O (designated herein as 2% W$_{20}$5EC NATROSOL 3); 2% W$_{20}$5EC, 0.5% NATROSOL 250H NF, and 97.5% diH$_2$O (designated herein as 2% W$_{20}$5EC NATROSOL 0.5); 2% W$_{20}$5EC, 2% METHOCEL A, and 96% diH$_2$O (designated herein as 2% W$_{20}$5EC METHOCEL A); 2% W$_{20}$5EC, 2% METHOCEL K, and 96% diH$_2$O (designated herein as 2% W$_{20}$5EC METHOCEL K); 2% NATROSOL, 0.1% X8PC, 0.1×PBS, 5 mM L-alanine, 5 mM Inosine, 10 mM Ammonium Chloride, and diH$_2$O (designated herein as 0.1% X8PC/GE+2% NATROSOL); 2% NATROSOL, 0.8% TRITON X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% NATROSOL); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% TRITON X-100, 54% Soybean Oil, and 20% diH$_2$O (designated herein as X8PC$_{10}$); 5% Cetylpyridinium Chloride, 8% TRITON X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1EC$_{0.02}$); 1% Cetylpyridinium Chloride, 5% TWEEN 20, 8% Glycerol, 64% MOBIL 1, and 22% diH$_2$O (designated herein as W$_{20}$5GC MOBIL 1); 7.2% TRITON X-100, 7.2%

Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% TRITON X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% TRITON X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

1. Aqueous Phase

In some embodiments, the emulsion comprises an aqueous phase. In certain preferred embodiments, the emulsion comprises about 5 to 50, preferably 10 to 40, more preferably 15 to 30, vol. % aqueous phase, based on the total volume of the emulsion (although other concentrations are also contemplated). In preferred embodiments, the aqueous phase comprises water at a pH of about 4 to 10, preferably about 6 to 8. The water is preferably deionized (hereinafter "DiH$_2$O"). In some embodiments, the aqueous phase comprises phosphate buffered saline (PBS). In some preferred embodiments, the aqueous phase is sterile and pyrogen free.

2. Oil Phase

In some embodiments, the emulsion comprises an oil phase. In certain preferred embodiments, the oil phase (e.g., carrier oil) of the emulsion of the present invention comprises 30-90, preferably 60-80, and more preferably 60-70, vol. % of oil, based on the total volume of the emulsion (although higher and lower concentrations also find use in emulsions described herein).

The oil in the nanoemulsion vaccine of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, CERAPHYLS, Decyl oleate, diisopropyl adipate, C$_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

In some embodiments, the oil phase comprises 3-15, and preferably 5-10 vol. % of an organic solvent, based on the total volume of the emulsion. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the methods of the present invention. Suitable organic solvents include, but are not limited to, organic phosphate based solvents or alcohols. In some preferred embodiments, non-toxic alcohols (e.g., ethanol) are used as a solvent. The oil phase, and any additional compounds provided in the oil phase, are preferably sterile and pyrogen free.

3. Surfactants and Detergents

In some embodiments, the emulsions further comprises a surfactant or detergent. In some preferred embodiments, the emulsion comprises from about 3 to 15%, and preferably about 10% of one or more surfactants or detergents (although other concentrations are also contemplated). While the present invention is not limited to any particular mechanism, it is contemplated that surfactants, when present in the emulsions, help to stabilize the emulsions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers.

The surfactant in the nanoemulsion vaccine of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Beta-sitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof. Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), BRIJ 35, BRIJ 56, BRIJ 72, BRIJ 76, BRIJ 92V, BRIJ 97, BRIJ 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, IGEPAL CA-630, IGEPAL CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, SPAN 20, SPAN 40, SPAN 60, SPAN 65, SPAN 80, SPAN 85, TERGITOL, Type 15-S-12, TERGITOL, Type 15-S-30, TERGITOL, Type 15-S-5, TERGITOL, Type 15-S-7, TERGITOL, Type 15-S-9, TERGITOL, Type NP-10, TERGITOL, Type NP-4, TERGITOL, Type NP-40, TERGITOL, Type NP-7, TERGITOL, Type NP-9, TERGITOL, TERGITOL, Type TMN-10, TERGITOL, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, TRITON CF-21, TRITON CF-32, TRITON DF-12, TRITON DF-16, TRITON GR-5M, TRITON QS-15, TRITON QS-44, TRITON X-100, TRITON X-102, TRITON X-15, TRITON X-151, TRITON X-200, TRITON X-207, TRITON X-100, TRITON X-114, TRITON X-165, TRITON X-305, TRITON X-405, TRITON X-45, TRITON X-705-70, TWEEN 20, TWEEN 21, TWEEN 40, TWEEN 60, TWEEN 61, TWEEN 65, TWEEN 80, TWEEN 81, TWEEN 85, TYLOXAPOL, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N,N-dimethyl-, chloride, Didecyl dimethyl ammonium chloride, 2-(2-(p-(Diisobutyl) cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl dimethyl benzyl ammonium chloride, Alkyl didecyl dimethyl ammonium chloride, Alkyl dimethyl benzyl ammonium chloride, Alkyl dimethyl benzyl ammonium chloride (C12-16), Alkyl dimethyl benzyl ammonium chloride (C12-18), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl (ethylbenzyl)ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl)octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with a particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4,1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, TRIZMA dodecyl sulfate, TWEEN 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semi-synthetic derivatives thereof, and combinations thereof.

The present invention is not limited to the surfactants disclosed herein. Additional surfactants and detergents useful in the compositions of the present invention may be ascertained from reference works (e.g., including, but not limited to, McCutheon's Volume 1: Emulsions and Detergents—North American Edition, 2000) and commercial sources.

4. Cationic Halogens Contaning Compounds

In some embodiments, the emulsions further comprise a cationic halogen containing compound. In some preferred embodiments, the emulsion comprises from about 0.5 to 1.0 wt. % or more of a cationic halogen containing compound, based on the total weight of the emulsion (although other concentrations are also contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), and cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen-containing compound is CPC, although the compositions of the present invention are not limited to formulation with any particular cationic containing compound.

5. Germination Enhancers

In other embodiments of the present invention, the nanoemulsions further comprise a germination enhancer. In some preferred embodiments, the emulsions comprise from about 1 mM to 15 mM, and more preferably from about 5 mM to 10 mM of one or more germination enhancing compounds (although other concentrations are also contemplated). In preferred embodiments, the germination enhancing compound is provided in the aqueous phase prior to formation of the emulsion. The present invention contemplates that when germination enhancers are added to the nanoemulsion compositions, the sporicidal properties of the nanoemulsions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the nanoemulsion preferentially occurs when the spores initiate germination.

In specific embodiments, it has been demonstrated that the emulsions utilized in the vaccines of the present invention have sporicidal activity. While the present invention is not limited to any particular mechanism and an understanding of the mechanism is not required to practice the present invention, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 (1950); and Halvorson and Church, Bacteriol Rev. 21:112 (1957)). L-alanine and L-proline have also been reported to initiate fungal spore germination (Yanagita, Arch Mikrobiol 26:329 (1957)). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate, which is the end product of glycolytic metabolism (Embden-Meyerhof Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle), which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104; herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the nanoemulsions utilized in some embodiments of the present invention. A candidate germination enhancer should meet two criteria for inclusion in the compositions of the present invention: it should be capable of being associated with the emulsions disclosed herein and it should increase the rate of germination of a target spore when incorporated in the emulsions disclosed herein. One skilled in the art can determine whether a particular agent has the desired function of acting as an germination enhancer by applying such an agent in combination with the nanoemulsions disclosed herein to a target and comparing the inactivation of the target when contacted by the admixture with inactivation of like targets by the composition of the present invention without the agent. Any agent that increases germination, and thereby decreases or inhibits the growth of the organisms, is considered a suitable enhancer for use in the nanoemulsion compositions disclosed herein.

In still other embodiments, addition of a germination enhancer (or growth medium) to a neutral emulsion composition produces a composition that is useful in inactivating bacterial spores in addition to enveloped viruses, Gram negative bacteria, and Gram positive bacteria for use in the vaccine compositions of the present invention.

6. Interaction Enhancers

In still other embodiments, nanoemulsions comprise one or more compounds capable of increasing the interaction of the compositions (i.e., "interaction enhancer") with target pathogens (e.g., the cell wall of Gram negative bacteria such as *Vibrio, Salmonella, Shigella* and *Pseudomonas*). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis (oxyethylenenitrilo)tetraacetic acid (EGTA) in a buffer (e.g., tris buffer)). It is understood that chelating agents are merely exemplary interaction enhancing compounds. Indeed, other agents that increase the interaction of the nanoemulsions used in some embodiments of the present invention with microbial agents and/or pathogens are contemplated. In particularly preferred embodiments, the interaction enhancer is at a concentration of about 50 to about 250 μM. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction of an emulsion with bacteria and thereby decreases or inhibits the growth of the bacteria, in comparison to that parameter in its absence, is considered an interaction enhancer.

In some embodiments, the addition of an interaction enhancer to nanoemulsion produces a composition that is useful in inactivating enveloped viruses, some Gram positive bacteria and some Gram negative bacteria for use in the vaccine compositions of the present invention.

7. Quaternary Ammonium Compounds

In some embodiments, nanoemulsions of the present invention include a quaternary ammonium containing compound. Exemplary quaternary ammonium compounds include, but are not limited to, Alkyl dimethyl benzyl ammonium chloride, didecyl dimethyl ammonium chloride, Alkyl dimethyl benzyl and dialkyl dimethyl ammonium chloride, N,N-Dimethyl-2-hydroxypropylammonium chloride polymer, Didecyl dimethyl ammonium chloride, n-Alkyl dimethyl benzyl ammonium chloride, n-Alkyl dimethyl ethylbenzyl ammonium chloride, Dialkyl dimethyl ammonium chloride, n-Alkyl dimethyl benzyl ammonium chloride, n-Tetradecyl dimethyl benzyl ammonium chloride monohydrate, n-Alkyl dimethyl benzyl ammonium chloride, Dialkyl dimethyl ammonium chloride, Hexahydro-1,3,5-tris(2-hydroxyethyl)-s-triazine, Myristalkonium chloride (and) Quat RNIUM 14, Alkyl bis(2-hydroxyethyl)benzyl ammonium chloride, Alkyl demethyl benzyl ammonium chloride, Alkyl dimethyl 3,4-dichlorobenzyl ammonium chloride, Alkyl dimethyl benzyl ammonium chloride, Alkyl dimethyl benzyl dimethylbenzyl ammonium, Alkyl dimethyl dimethybenzyl ammonium chloride, Alkyl dimethyl ethyl ammonium bromide, Alkyl dimethyl ethyl ammonium bromide, Alkyl dimethyl ethylbenzyl ammonium chloride, Alkyl dimethyl isopropylbenzyl ammonium chloride, Alkyl trimethyl ammonium chloride, Alkyl 1 or 3 benzyl-1-(2-hydroxethyl)-2-imidazolinium chloride, Dialkyl methyl benzyl ammonium chloride, Dialkyl dimethyl ammonium chloride, Didecyl dimethyl ammonium chloride, 2-(2-(p-(Diisobutyl)cresosxy) ethoxy)ethyl dimethyl benzyl ammonium chloride, 2-(2-(p-(Diisobutyl)phenoxy)ethoxy)ethyl dimethyl benzyl ammonium chloride, Dioctyl dimethyl ammonium chloride, Dodecyl bis(2-hydroxyethyl)octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl quats, and Trimethyl dodecylbenzyl ammonium chloride.

8. Other Components

In some embodiments, a nanoemulsion comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion (e.g., used to inactivate a pathogen and/or generation of an immunogenic composition of the present ivention) are described below. Additionally, a number of specific, although exemplary, formulation recipes are also set forth below.

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen (e.g., a pathogen). In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oy a sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1B. These particular formulations may be found in U.S. Pat. No. 5,700,679 (NN); U.S. Pat. Nos. 5,618,840; 5,549,901 ($W_{80}8P$); and U.S. Pat. No. 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1B

| | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride | 3.2:1 |

TABLE 1B-continued

| | Oil Phase Formula | Water to Oil Phase Ratio (Vol/Vol) |
|---|---|---|
| SS | 4 ml Peppermint oil<br>554 g Soybean oil<br>86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri(N-butyl)phosphate:TRITON X-100:soybean oil also may be varied.

Although Table 1B lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOXAPOL, about 8 vol. % of ethanol, about 1 vol. % of cetylpyridinium chloride (CPC), about 60 to 70 vol. % of oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, about 10 mM ammonium chloride, about 57.6 vol. % of soybean oil, and the remainder of 1×PBS (designated herein as 90% X2Y2EC/GE).

In some embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of $DiH_2O$ (designated herein as $W_{80}5EC$).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of $DiH_2O$ (designated herein as $W_{20}5EC$).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., $DiH_2O$ or PBS). For example, the present invention contemplates formulations comprising about 2 vol. % of TRITON X-100, about 8 vol. % of ethanol, about 64 vol. % of soybean oil, and about 26 vol. % of $DiH_2O$ (designated as X2E). In other similar embodiments, a nanoemulsion comprises about 3 vol. % of TRITON X-100, about 8 vol. % of ethanol, about 64 vol. % of soybean oil, and about 25 vol. % of $DiH_2O$ (designated herein as X3E). In still further embodiments, the formulations comprise about 4 vol. % TRITON of X-100, about 8 vol. % of ethanol, about 64 vol. % of soybean oil, and about 24 vol. % of $DiH_2O$ (designated herein as X4E). In yet other embodiments, a nanoemulsion comprises about 5 vol. % of TRITON X-100, about 8 vol. % of ethanol, about 64 vol. % of soybean oil, and about 23 vol. % of $DiH_2O$ (designated herein as X5E). In some embodiments, a nanoemulsion comprises about 6 vol. % of TRITON X-100, about 8 vol. % of ethanol, about 64 vol. % of soybean oil, and about 22 vol. % of $DiH_2O$ (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of $DiH_2O$ (designated herein as X8E). In still further embodiments, a nanoemulsion comprises about 8 vol. % of TRITON X-100, about 8 vol. % of ethanol, about 64 vol. % of olive oil, and about 20 vol. % of $DiH_2O$ (designated herein as X8E O). In yet another embodiment, a nanoemulsion comprises 8 vol. % of TRITON X-100, about 8 vol. % ethanol, about 1 vol. % CPC, about 64 vol. % of soybean oil, and about 19 vol. % of $DiH_2O$ (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., $DiH_2O$ or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of $DiH_2O$ (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of $DiH_2O$ (designated herein as X2Y2PC STS1). In another similar embodiment, a nanoemulsion comprises about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of $DiH_2O$ (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of $DiH_2O$ (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of $DiH_2O$ (designated herein as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., $DiH_2O$ or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of $DiH_2O$ (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., $DiH_2O$ or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 μM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of $DiH_2O$ (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of $DiH_2O$ (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of $DiH_2O$ (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1-x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, a nanoemulsion comprises about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsions that find use (e.g., to inactivate and/or neutralize a pathogen, and for generating an immune response in a subject (e.g., for use as a vaccine)) in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% TRITON X-100, 0.08% Glycerol, 0.01% Cetylpyridinium Chloride, 99% Butter, and 0.83% diH$_2$O (designated herein as 1% X8GC Butter); 0.8% TRITON X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% NATROSOL 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, a nanoemuslion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% NATROSOL 250H NF, and 96% diH$_2$O (designated herein as 2% W$_{20}$5EC NATROSOL 2, also called 2% W$_{20}$5EC GEL); 2% W$_{20}$5EC, 1% NATROSOL 250H NF, and 97% diH$_2$O (designated herein as 2% W$_{20}$5EC NATROSOL 1); 2% W$_{20}$5EC, 3% NATROSOL 250H NF, and 95% diH$_2$O (designated herein as 2% W$_{20}$5EC NATROSOL 3); 2% W$_{20}$5EC, 0.5% NATROSOL 250H NF, and 97.5% diH$_2$O (designated herein as 2% W$_{20}$5EC NATROSOL 0.5); 2% W$_{20}$5EC, 2% METHOCEL A, and 96% diH$_2$O (designated herein as 2% W$_{20}$5EC METHOCEL A); 2% W$_{20}$5EC, 2% METHOCEL K, and 96% diH$_2$O (designated herein as 2% W$_{20}$5EC METHOCEL K); 2% NATROSOL, 0.1% X8PC, 0.1×PBS, 5 mM L-alanine, 5 mM Inosine, 10 mM Ammonium Chloride, and diH$_2$O (designated herein as 0.1% X8PC/GE+2% NATROSOL); 2% NATROSOL, 0.8% TRITON X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% NATROSOL); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as $W_{20}5EC_{0.1}F$); 0.1% Cetylpyridinium Chloride, 5% TWEEN 20, 10% Ethanol, 64% Soybean Oil, and 20.9% diH$_2$O (designated herein as $W_{20}5EC_{0.1}$); 10% Cetylpyridinium Chloride, 8% Tributyl Phosphate, 8% TRITON X-100, 54% Soybean Oil, and 20% diH$_2$O (designated herein as $X8PC_{10}$); 5% Cetylpyridinium Chloride, 8% TRITON X-100, 8% Tributyl Phosphate, 59% Soybean Oil, and 20% diH$_2$O (designated herein as $X8PC_5$); 0.02% Cetylpyridinium Chloride, 0.1% TWEEN 20, 10% Ethanol, 70% Soybean Oil, and 19.88% diH$_2$O (designated herein as $W_{20}0.1EC_{0.02}$); 1% Cetylpyridinium Chloride, 5% TWEEN 20, 8% Glycerol, 64% MOBIL 1, and 22% diH$_2$O (designated herein as $W_{20}5GC$ MOBIL 1); 7.2% TRITON X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% TRITON X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% TRITON X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while possessing potency against a broad range of microorganisms including bacteria, fungi, viruses, and spores. While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprises a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 µM-20 mM)); and amino acids (e.g., L-alanine (50 µM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl)ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysilypropyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

Therapeutics and Prophylactics

Furthermore, in preferred embodiments, a composition of the present invention induces (e.g., when administered to a subject) both systemic and mucosal immunity. Thus, in some preferred embodiments, administration of a composition of the present invention to a subject results in protection against an exposure to one or a plurality of pathogens.

In some embodiments, the present invention provides a composition comprising a nanoemulsion and one or a plurality of immunogens to serve as a mucosal vaccine. In some embodiments, this material can easily be produced. The ability to produce this formulation rapidly and administer it via mucosal (e.g., nasal) instillation provides a vaccine that can be used in large-scale administrations (e.g., to a population of a town, village, city, state or country).

In some preferred embodiments, the present invention provides a composition for generating an immune response comprising a nanoemulsion and one or a plurality of immunogens (e.g., a purified, isolated or synthetic protein or derivative, variant, or analogue thereof from one or more serotypes of HBV).

The present invention is not limited by the plurality of immunogens utilized. For example, in some embodiments, the plurality of immunogens comprises immunogenic protein antigens from HIV (e.g., gp120) to serve as a mucosal vaccine. This material can easily be produced with NE and HIV protein (e.g., viral-derived gp120, live-virus-vector-derived gp120 and gp 160, recombinant mammalian gp120, recombinant denatured antigens, small peptide segments of gp120 and gp41, V3 loop peptides, and induces both mucosal and systemic immunity. The ability to produce this formulation rapidly and administer it via mucosal (e.g., nasal or vaginal) instillation provides a vaccine that can be used in large-scale administrations (e.g., to a population of a town, village, city, state or country).

In some embodiments, one or a plurality of immunogens comprises one or more strains of orthopox virus (e.g., in a composition comprising a NE and immunogen (e.g., orthopox virus inactivated by the nanoemulsion). Each orthopox virus family member alone, or in combination with another family member, may be used to generate a composition comprising a NE and an immunogen (e.g., used to generate an immune response) of the present invention. Orthopox virus family member include, but are not limited to, variola virus, vaccinia virus, cowpox, monkeypox, gergilpox, camelpox, and others. The present invention is not limited by the strain of vaccinia virus used. Indeed, a variety of vaccinia virus strains are contemplated to be useful in the present invention including, but not limited to, classical strains of vaccinia virus (e.g., EM-63, Lister, New York City Board of Health, Elestree, and Temple of Heaven strains), attenuated strains (e.g., Ankara), non-replicating strains, modified strains (e.g., genetically or mechanically modified strains (e.g., to become more or less virulent)), Copenhagen strain, modified vaccinia Ankara, New York vaccinia virus, Vaccinia Virus$_{WR}$ and Vaccinia Virus$_{WR-Luc}$, or other serially diluted strain of vaccinia virus. A composition comprising a NE and one or a plurality of immunogens may comprise one or more strains of vaccinia virus and/or other type of orthopox virus. Additionally, a composition comprising a NE and one or a plurality of immunogens may comprise one or more strains of vaccinia virus, and, in addition, one or more strains of a non-vaccinia virus immunogen or immunogenic epitope thereof (e.g., a bacteria (e.g., B. anthracis) or immunogenic epitope thereof (e.g., recombinant protective antigen) or a virus (e.g., West Nile virus, Avian Influenza virus, Ebola virus, HSV, HPV, HCV, HIV, etc.) or an immunogenic epitope thereof (e.g., gp120)).

In some embodiments, the immunogen may comprise one or more antigens derived from a pathogen (e.g., orthopox virus). For example, in some embodiments, the immunogen is a purified, recombinant, synthetic, or otherwise isolated protein (e.g., added to the NE to generate an immunogenic composition). Similarly, the immunogenic protein may be a derivative, analogue or otherwise modified (e.g., PEGylated) form of a protein from a pathogen.

In some embodiments, one or a plurality of immunogens comprises one or more strains of Bacillus or immunogenic proteins derived therefrom. For example, 89 different strains of B. anthracis have been identified, ranging from virulent Ames and Vollum strains with biological warfare and bioterrorism applications to benign Sterne strain used for inoculations (See, e.g., Easterday et al., J Clin Microbiol. 2005 43(4): 1995-7). The strains differ in presence and activity of various genes, determining their virulence and production of antigens and toxins. Any one of these or yet to be identified or generated strains may be used in an immunogenic composition comprising a NE of the present invention.

In some embodiments, the immunogen may comprise one or more antigens derived from a pathogen (e.g., B. anthracis). For example, in some embodiments, the immunogen is a purified, recombinant, synthetic, or otherwise isolated protein (e.g., added to the NE to generate an immunogenic composition). Similarly, the immunogenic protein may be a derivative, variant, analogue or otherwise modified form of a protein from a pathogen. The present invention is not limited by the type of protein (e.g., derived from bacteria of the genus Bacillus) used for generation of an immunogenic composition of the present invention. Indeed, a variety of immunogenic proteins may be used including, but not limited to, protective antigen (PA), lethal factor (LF), edema factor (EF), PA degradation products (See, e.g., Farchaus, J., et al., Applied & Environmental Microbiol., 64(3):982-991 (1998)), as well as analogues, derivatives and modified forms thereof.

For example, Bacillus proteins of the present invention may be used in their native conformation, or more preferably, may be modified for vaccine use. These modifications may either be required for technical reasons relating to the method of purification, or they may be used to biologically inactivate one or several functional properties of the Bacillus proteins (e.g., that would otherwise be toxic). Thus the invention encompasses derivatives of *Bacillus* proteins that may be, for example, mutated proteins (e.g., that has undergone deletion, addition or substitution of one or more amino acids using well known techniques for site directed mutagenesis or any other conventional method).

Antigens (e.g., protein antigens (e.g., recombinant protective antigen (PA))) of the present invention may be modified by chemical methods during a purification process to render the proteins stable and monomeric. One method to prevent oxidative aggregation of a protein is the use of chemical modifications of the protein's thiol groups. In a first step the disulphide bridges are reduced by treatment with a reducing agent such as DTT, β-mercaptoethanol, or gluthatione. In a second step the resulting thiols are blocked by reaction with an alkylating agent (e.g., the protein can be carboxyamidated/carbamidomethylated using iodoacetamide).

Each *Bacillus* family member alone, or in combination with another family member, may be used to generate a composition comprising a NE and plurality of immunogens (e.g., used to generate an immune response) of the present invention. A composition comprising a NE and plurality of immunogens may comprise one or more strains of *B. anthracis*. Additionally, a composition comprising a NE and plurality of immunogens may comprise one or more strains of *B. anthracis*, and, in addition, one or more strains of a non-*B. anthracis* immunogen (e.g., a virus such as West Nile virus, Avian Influenza virus, Ebola virus, HSV, HPV, HCV, HIV, etc. or an immunogenic epitope thereof (e.g., gp120)).

The present invention is not limited by the type (e.g., serotype, group, or Glade) of HIV used or immunogenic protein derived therefrom. For example, there are currently two types of HIV: HIV-1 and HIV-2. Both types are transmitted by sexual contact, through blood, and from mother to child, and they appear to cause clinically indistinguishable AIDS. However, it seems that HIV-2 is less easily transmitted, and the period between initial infection and illness is longer in the case of HIV-2. Worldwide, the predominant virus is HIV-1, and generally when people refer to HIV without specifying the type of virus they will be referring to HIV-1. The relatively uncommon HIV-2 type is concentrated in West Africa and is rarely found elsewhere.

Different levels of HIV classification exist. Each type is divided into groups, and each group is divided into subtypes and circulating recombinant forms (CRFs). The strains of HIV-1 can be classified into three groups: the "major" group M, the "outlier" group 0 and the "new" group N.

Within group M there are known to be at least nine genetically distinct subtypes (or clades) of HIV-1. These are subtypes A, B, C, D, F, G, H, J and K.

Any one of these or yet to be identified or generated serotypes, groups, or clades may be used in an immunogenic composition comprising a NE of the present invention.

In some embodiments, one or a plurality of immunogens may comprise one or more antigens derived from a pathogen (e.g., HIV). For example, in some embodiments, the immunogen is a purified, recombinant, synthetic, or otherwise isolated protein (e.g., added to the NE to generate an immunogenic composition). Similarly, the immunogenic protein may be a derivative, analogue or otherwise modified form of a protein from a pathogen. The present invention is not limited by the type of protein (e.g., derived from HIV) used for generation of an immunogenic composition of the present invention. Indeed, a variety of immunogenic proteins may be used including, but not limited to, gp160, gp120, gp41, Tat, and Nef; as well as analogues, derivatives and modified forms thereof.

For example, HIV proteins of the present invention may be used in their native conformation, or more preferably, may be modified for vaccine use. These modifications may either be required for technical reasons relating to the method of purification, or they may be used to biologically inactivate one or several functional properties of HIV protein. Thus the invention encompasses derivatives of HIV proteins which may be, for example mutated proteins (e.g., that has undergone deletion, addition or substitution of one or more amino acids using well known techniques for site directed mutagenesis or any other conventional method.

For example, a HIV protein may be mutated so that it is biologically inactive while maintaining its immunogenic epitopes (See, e.g., Clements, Virology 235: 48-64, 1997).

Additionally, HIV proteins of the present invention may be modified by chemical methods during the purification process to render the proteins stable and monomeric. One method to prevent oxidative aggregation of a HIV protein is the use of chemical modifications of the protein's thiol groups. In a first step the disulphide bridges are reduced by treatment with a reducing agent such as DTT, β-mercaptoethanol, or gluthatione. In a second step the resulting thiols are blocked by reaction with an alkylating agent (e.g., the protein can be carboxyamidated/carbamidomethylated using iodoacetamide).

Each HIV serotype, group or Glade alone, or in combination with another family member, may be used to generate a composition comprising a NE and an immunogen (e.g., used to generate an immune response) of the present invention. A composition comprising a NE and immunogen may comprise one or more serotypes, groups or clades of HIV. Additionally, a composition comprising a NE and immunogen may comprise one or more serotypes, groups or clades of HIV, and, in addition, one or more strains of a non-HIV immunogen (e.g., a virus such as West Nile virus, Avian Influenza virus, Ebola virus, HSV, HPV, HCV, etc. or an immunogenic epitope thereof).

When administered to a subject, a composition of the present invention stimulates an immune response against one or a plurality of immunogens within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and plurality of immunogens) provides total or partial immunity to the subject (e.g., from signs, symptoms or conditions of a disease (e.g., to a plurality of pathogens from which the immunogens are derrived)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to a NE comprising one or a plurality of immunogens of the present invention (e.g., immune responses that exhibit increased specificity and reactivity towards one or a plurality of pathogens from which the immunogens are derived). Thus, in some embodiments, the compositions and methods of the present invention are used prophylactically or therapeutically to prevent or attenuate a sign, symptom or condition associated with one or a plurality of pathogens.

In some embodiments, a composition comprising a nanoemulsion and one or a plurality of immunogens is administered alone. In some embodiments, a composition comprising a nanoemulsion and one or a plurality of immunogens comprises one or more other agents (e.g., a pharmaceutically acceptable carrier, adjuvant, excipient, and the like). In some embodiments, a composition for stimulating an immune response of the present invention is administered in a manner to induce a humoral immune response. In some embodiments, a composition for stimulating an immune response of the present invention is administered in a manner to induce a cellular (e.g., cytotoxic T lymphocyte) immune response, rather than a humoral response. In some embodiments, a composition comprising a NE and an immunogen of the present invention induces both a cellular and humoral immune response.

In some embodiments, the immunogen may comprise one or more antigens derived from one or a plurality of immunogens. For example, in some embodiments, the immunogen is a purified, recombinant, synthetic, or otherwise isolated protein (e.g., added to a nanoemulsion to generate an immunogenic composition). Similarly, the immunogenic protein may be a derivative, analogue or otherwise modified (e.g., PEGylated) form of a protein.

The present invention is not limited by the particular formulation of a composition comprising a nanoemulsion and a plurality of immunogens of the present invention. Indeed, a composition comprising a nanoemulsion and one or a plurality of immunogens of the present invention may comprise one or more different agents in addition to the nanoemulsion and plurality of immunogens. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion and one or a plurality of immunogens of the present invention comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune respone (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a NE and immunogen). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising a NE and one or a plurality of immunogens. However, in other embodiments, the present invention provides a method of stimulating a Th2-type immune response in a subject (e.g., if balancing of a T cell mediated response is desired) comprising administering to a subject a composition comprising a NE and one or a plurality of immunogens. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4): 392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057, 540; Kensil, Crit. Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a NE and one or a plurality of immunogens, or, the adjuvant may be formulated with carriers, for example liposomes, or metallic salts (e.g., aluminium salts (e.g., aluminium hydroxide)) prior to combining with or co-administration with a composition comprising a NE and an immunogen.

In some embodiments, a composition comprising a NE and an immunogen comprises a single adjuvant. In other embodiments, a composition comprising a NE and an immunogen comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE and an immunogen of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the muco adhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a NE and an immunogen of the present invention can be used therapeutically (e.g., to enhance an immune response) or as a prophylactic (e.g., for immunization (e.g., to prevent signs or symptoms of disease)). A composition comprising a NE and an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a NE and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a sujbect to be immunized. In some embodiments, a nebulized or aerosolized composition comprising a NE and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a NE and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising a NE and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a NE and immunogen of the present invention).

For example, in some embodiments, a composition comprising a NE and an immunogen is administered to a mucosal surface of a subject in either a priming or boosting vaccination regime. Alternatively, in some embodiments, a composition comprising a NE and an immunogen is administered systemically in either a priming or boosting vaccination regime. In some embodiments, a composition comprising a NE and an immunogen is administered to a subject in a priming vaccination regimen via mucosal administration and a boosting regimen via systemic administration. In some embodiments, a composition comprising a NE and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140: 3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a NE and an immunogen of the present invention may be used to protect and/or treat a subject susceptible to, or suffering from, a disease by means of administering a compositions comprising a NE and an immunogen by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., HBV). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl)pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (SPAN 80); p-isooctyl polyoxyethylene-phenol polymer (TRITON WR-1330); polyoxyethylene sorbitan tri-oleate (TWEEN 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the NE and immunogen of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a NE and an immunogen is co-administered with one or more antibiotics. For example, one or more antibiotics may be administered with, before and/or after administration of a composition comprising a NE and an immunogen. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a NE and one or a plurality of immunogens with one or more additional active and/or immunostimulatory agents (e.g., a composition comprising a NE and a different immunogen, an antibiotic, antioxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a NE and one or a plurality of immunogens is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of a composition comprising a NE and immunogen of the present invention) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a composition comprising a NE and one or a plurality of immunogens of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

In preferred embodiments, a composition comprising a NE and an immunogen of the present invention comprises a suitable amount of the immunogen to induce an immune response in a subject when administered to the subject. In preferred embodiments, the immune response is sufficient to provide the subject protection (e.g., immune protection) against a subsequent exposure to the immunogen or the microorganism (e.g., bacteria or virus) from which the immunogen was derived. The present invention is not limited by the amount of immunogen used. In some preferred embodiments, the amount of immunogen (e.g., virus or bacteria neutralized by the NE, or, recombinant protein) in a composition comprising a NE and immunogen (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration. Procedures for determining the appropriate amount of immunogen administered to a subject to elicit an immune response (e.g., a protective immune response (e.g., protective immunity)) in a subject are well known to those skilled in the art.

In some embodiments, it is expected that each dose (e.g., of a composition comprising a NE and one or a plurality of immunogens (e.g., administered to a subject to induce an immune response (e.g., a protective immune response (e.g., protective immunity))) comprises 0.05-5000 µg of each immunogen (e.g., recombinant and/or purified protein), in some embodiments, each dose will comprise 1-500 µg, in some embodiments, each dose will comprise 350-750n, in some embodiments, each dose will comprise 50-200 µg, in some embodiments, each dose will comprise 25-75 µg of each immunogen (e.g., recombinant and/or purifed protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a NE and one or a plurality of antigens (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose In some embodiments, when a NE of the present invention is utilized to inactivate a live microorganism (e.g., virus (e.g., HIV)), it is expected that each dose (e.g., administered to a subject to induce and immune response)) comprises between 10 and $10^9$ pfu of the virus per dose; in some embodiments, each dose comprises between $10^5$ and $10^8$ pfu of the virus per dose; in some embodiments, each dose comprises between $10^3$ and $10^5$ pfu of the virus per dose; in some embodiments, each dose comprises between $10^2$ and $10^4$ pfu of the virus per dose; in some embodiments, each dose comprises 10 pfu of the virus per dose; in some embodiments, each dose comprises $10^2$ pfu of the virus per dose; and in some embodiments, each dose comprises $10^4$ pfu of the virus per dose. In some embodiments, each dose comprises more than $10^9$ pfu of the virus per dose. In some preferred embodiments, each dose comprises $10^3$ pfu of the virus per dose.

In some embodiments, when a NE of the present invention is utilized to inactivate a live microorganism (e.g., a population of bacteria (e.g., of the genus *Bacillus* (*B. anthracis*))), it is expected that each dose (e.g., administered to a subject to induce and immune response)) comprises between 10 and $10^{10}$ bacteria per dose; in some embodiments, each dose comprises between $10^5$ and $10^8$ bacteria per dose; in some embodiments, each dose comprises between $10^3$ and $10^5$ bacteria per dose; in some embodiments, each dose comprises between $10^2$ and $10^4$ bacteria per dose; in some embodiments, each dose comprises 10 bacteria per dose; in some embodiments, each dose comprises $10^2$ bacteria per dose; and in some embodiments, each dose comprises $10^4$ bacteria per dose. In some embodiments, each dose comprises more than $10^{10}$ bacteria per dose. In some embodiments, each dose comprises $10^3$ bacteria per dose.

The present invention is not limited by the amount of NE used to inactivate live microorganisms (e.g., a virus (e.g., one or more types of HIV)). In some embodiments, a 0.1%-5% NE solution is used, in some embodiments, a 5%-20% NE solution is used, in some embodiments, a 20% NE solution is used, and in some embodiments, a NE solution greater than 20% is used order to inactivate a pathogenic microorganism. In some embodiments, a 10% NE solution is used.

Similarly, the present invention is not limited by the duration of time a live microorganism is incubated in a NE of the present invention in order to become inactivated. In some embodiments, the microorganism is incubated for 1-3 hours in NE. In some embodiments, the microorganism is incubated for 3-6 hours in NE. In some embodiments, the microorganism is incubated for more than 6 hours in NE. In preferred embodiments, the microorganism is incubated for 3 hours in NE (e.g., a 10% NE solution). In some embodiments, the incubation is carried out at 37° C. In some embodiments, the incubation is carried out at a temperature greater than or less than 37° C. The present invention is also not limited by the amount of microorganism used for inactivation. The amount of microorganism may depend upon a number of factors including, but not limited to, the total amount of immunogenic composition (e.g., NE and immunogen) desired, the concentration of solution desired (e.g., prior to dilution for administration), the microorganism and the NE. In some preferred embodiments, the amount of microorganism used in an inactivation procedure is that amount that produces the desired amount of immunogen (e.g., as described herein) to be administered in a single dose (e.g., diluted from a concentrated stock) to a subject.

In some embodiments, a composition comprising a NE and one or more immunogens of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.1-50% of the NE and one or more immunogens present in the concentrated composition. In some preferred embodiments, a subject is administered in a single dose a composition comprising 1% of the NE and one or more immunogens present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and one or more immunogens of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject.

The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

A composition comprising an immunogen of the present invention finds use where the nature of the infectious and/or disease causing agent (e.g., for which protective immunity is sought to be elicited) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of (e.g., via immunization with an infectious and/or disease causing HIV or HIV-like agent neutralized via a NE of the present invention) infections associated with an emergent infectious and/or disease causing agent yet to be identified (e.g., isolated and/or cultured from a diseased person but without genetic, biochemical or other characterization of the infectious and/or disease causing agent).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of mucosal and other routes of delivery. As is readily apparent, the compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising a NE and one or more immunogens. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a NE and one or more immunogens in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXAMPLES

The following examples serve to illustrate certain preferred embodiments and aspects of the present invention and are not to be construed as limiting the scope thereof.

In the experimental disclosure which follows, the following abbreviations apply: eq (equivalents); μ (micron); M (Molar); μM (micromolar); mM (millimolar); N (Normal); mol (moles); mmol (millimoles); pmol (micromoles); nmol (nanomoles); g (grams); mg (milligrams); μg (micrograms); ng (nanograms); L (liters); ml (milliliters); μl (microliters); cm (centimeters); mm (millimeters); μm (micrometers); nM (nanomolar); ° C. (degrees Centigrade); and PBS (phosphate buffered saline).

Example 1

Compositions Comprising a Trivalent Nanoemulsion-Based Vaccine Against *Bacillus anthracia, Yersinia pestis,* and *Clostridium botulinum* and Methods of Using the Same Materials and Methods Vaccination. Anesthetized CD-1 mice were immunized with two nasal administrations of either monovalent or with a trivalent vaccine composed of the combination of recombinant proteins (20 μg of each antigen): PA (protective antigen) of *Bacillus anthracis*, rLcrV (or LcrV10) protein of *Yersinia. pestis* and rHCR/A1 (fragment of *Clostridium botulinum* neurotoxin) mixed with 20% $W_{80}5EC$ (10 ul). Control immunizations were performed with antigens suspended in PBS, or with intramuscular injection of antigens adsorbed onto aluminum hydroxide adjuvant (alum, 0.5 μg/ml, 50 ul).

Antibody response. To analyze humoral immunity, serum samples were collected at 2-4 weeks intervals over a course of time. Bronchoalveolar lavage fluid (BAL), spleen and cardiac blood were collected at the termination of animals. Serum and BAL antigen specific IgG and secretory IgA titers as well as IgG subclass determination were performed using ELISA. Cellular immunity. To assess cellular responses, splenocytes were isolated from immunized mice and stimulated in vitro with specific antigen for 72 hours days. Antigen specific cytokine production was assayed in culture supernatants using specific cytokine detection kit (R&D) or Lumiex assays.

Antigens and adjuvant. HCR/A1 and LcrV provided non-commercially by Dr. Joseph Barbieri, Medical College of Wisconsin, and Dr. Olaf Schneewind, University of Chicago, respectively. PA was purchased from BEI Resources, Manassas, Va. W805EC was provided by the NANOBIO Corporation, Ann Arbor, Mich. Polyacrylamide gel electrophoresis (PAGE) was performed on each antigen prior to mixing with nanoemulsion (See FIG. 1). Each antigen appeared to be intact and without contamination.

Immunogenic composition formulation. A trivalent, nanoemulsion-adjuvanted vaccine was designed for nasal administration. Immune responses in mice were evaluated after intranasal (i.n) immunization with either monovalent or with a trivalent vaccine composed of the combination of recombinant proteins: PA (protective antigen) of *B. anthracis*, rHCR/A1 (fragment of *C. botulinum* neurotoxin) and rLcrV (or LcrV10) protein of *Y. pestis* administered with an oil-in-water nanoemulsion (NE, $W_{80}5EC$ formulation) adjuvant. CD-1 mice were immunized with two IN administrations of either trivalent vaccine comprised of 20 µg of each recombinant antigen or with a monovalent vaccine containing a single antigen mixed with 20% NE adjuvant. For intramuscular (IM) immunizations, mice were injected with antigens adsorbed on aluminum hydroxide (alum). For assessment of antibody response, serum was collected at multiple time points. Spleens and cardiac blood were collected at termination of the experiment at 19 weeks. Serum antigen specific IgG and IgA subclass titers were determined by ELISA. Cellular response was characterized in vitro by the antigen-specific cytokine expression in splenocytes from immunized mice Example 2

Characterization of Immune Response from Trivalent Nanoemulsion-Based Mucosal Vaccine Against *Bacillus anthracia, Yersinia pestis*, and *Clostridium botulinum*

The immunogenicity of trivalent vaccines against HCR/A1, PA and either full length LcrV protein (See FIG. 1A) or truncated LcrV10 protein (See FIG. 1B) mixed with NE were tested by the analysis of antigen-specific serum IgG in immunized mice. Development of immune response after nasal immunization with trivalent vaccine composed of PA/HCR/A1 and full length LcrV protein in shown in FIG. 2. Single intranasal (IN) immunization produced rapid and significant IgG response to all antigens. The anti-HCR/A1 response was 10 to 15 fold lower than PA and LcrV antigens. After boost the IgG levels reached over $10^6$ titers which were sustained for 5 months without significant decrease in antibody levels. Immunizations with antigens in PBS (without combining with nanoemulsion) did not produce detectable immune responses.

Development of immune response after nasal immunization with trivalent vaccine composed of PA/HCR/A1 and truncated LcrV10 protein is shown in FIG. 2B. As with full length LCRV protein, single IN immunization produced rapid significant IgG response to all antigens. Again, the anti-HCR/A1 response was 10 to 15 fold lower than PA and LcrV10 antigens. After boost the IgG levels reached over $10^6$ titers which were sustained for 5 months without significant decrease in antibody levels. Immunizations with antigens in PBS (without combining with nanoemulsion) did not produce detectable immune responses.

Thus, the present invention provides that both vaccine formulations were immunogenic and produced high anti-PA and anti-LcrV and LcrV10 antibody response surpassing $10^6$ titers. Antibody response to HCR/A1 protein was consistently over 10 fold lower than response to PA, LcrV, and LcrV10 even in increased concentration of antigen.

Antigen-specific immune responses in trivalent versus monovalent vaccines is shown in FIG. 3. To determine if combining antigens affect their immunogenicity the efficacy of trivalent and monovalent vaccines was analyzed. Comparison of IgG titers in trivalent versus monovalent vaccines indicated that combing the antigens did not affect their immunogenicity (e.g., either by combining the plurality of antigens with nanoemulsion or by suppressing the specific immune response generated by each antigen). Thus, the present invention provides that immune responses produced by trivalent and monovalent NE-based nasal vaccines demonstrated that combining all three proteins does not affect immunogenicity of any of the individual antigens (See FIG. 3). In each case the trivalent vaccine was capable of producing nearly identical antigen specific titer level to the corresponding monovalent vaccine, demonstrating that trivalency does not reduce the immunogenicity of the individual antigens.

Immunogenicity of nasal NE-adjuvanted trivalent vaccine was compared to that of intramuscular injected alum-based vaccine by measurement of serum antigen specific titers 19 weeks after prime. The NE-adjuvanted trivalent vaccines produced immune responses comparable to intramuscular injection of conventional alum-based vaccines for each antigen tested (See FIG. 4). The present invention provides that, based upon the comparison of IgG titers elicited by NE-based vaccines with conventional alum-adjuvanted vaccines, mucosal vaccination produced antibody titers comparable with intramuscular vaccines.

Figure 5:
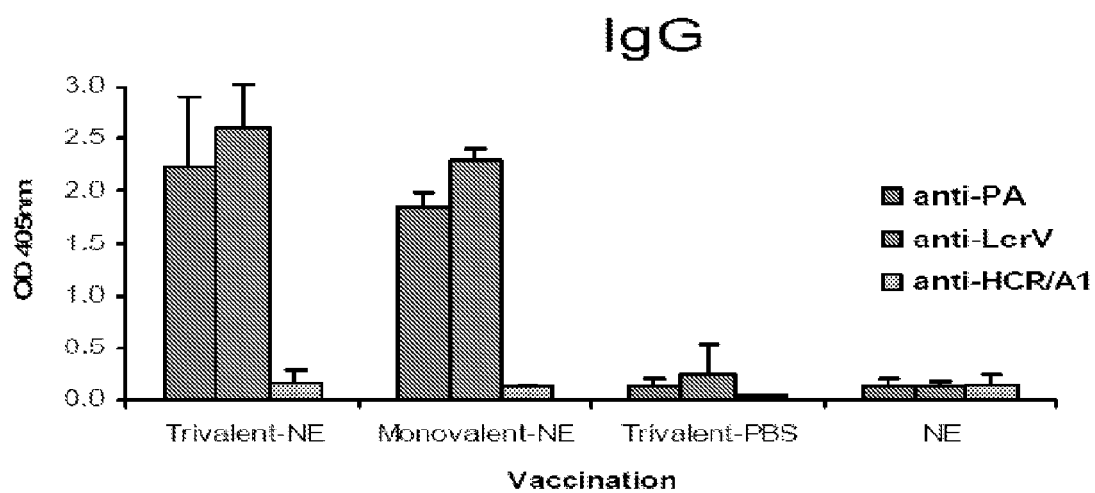
FIG. 5 shows the mucosal response following nasal immunization with NE-based vaccines for mucosal IgG shown in (A) and IgA shown in (B).
Figure 5:
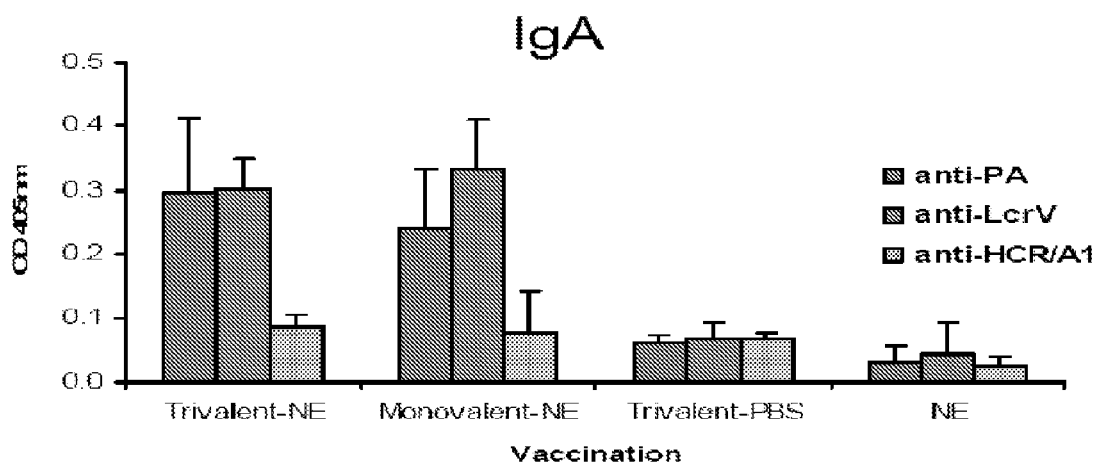

FIG. 5 shows that nasal immunization with both trivalent vaccines produced mucosal immunity. The antigen-specific secretory IgA and IgG were detected in Bronchoalveolar lavage fluid (BAL) from mice obtained up to 5 months after vaccination. Nasal immunizations with NE-adjuvanted trivalent vaccines were capable of producing antigen-specific mucosal IgG (See FIG. 5A) and IgA (See FIG. 5B) in brochial secretions to the same degree as the corresponding monovalent vaccines.

Figure 6:
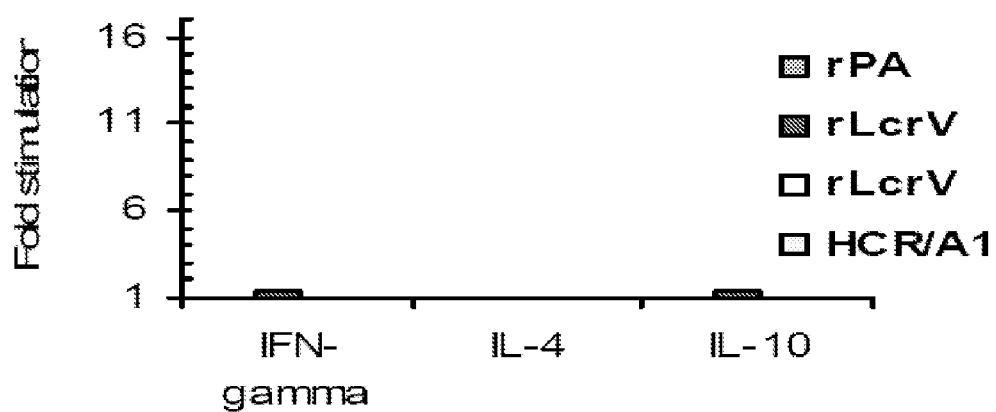
FIG. 6 shows the Th-1 polarization of the immune response of subjects administered a trivalent vaccine of the invention.

In order to analyze the cellular response in mice immunized with trivalent nanoemulsion-based vaccines, cytokine levels were monitored in spenocytes of immunized mice. The pattern of antigen specific Th1- and Th-2 type cytokine expression in vitro shows 5 to 16 fold increase of INF-γ, and significantly lower levels of IL-4, without significant effect on other cytokines (See FIG. 6). The antigen specific induction of IFN-γ, which is consider a hallmark of TH-1 response and lack of IL-4 indicated that immunization with the trivalent vaccine produced a Th-1 biased cellular response. Neither LcrV10 nor LcrV10 mutant had an effect on IL-10 synthesis. Mock immunization with nanoemulsion alone did not produce cytokine responses in splenic lymphocytes. Thus, the present invention provides that immunization with a trivalent vaccine of the invention induced a mixed Th1-Th2 immune response with a functional bias toward Th-1 cell mediated immunity.

Figure 7:
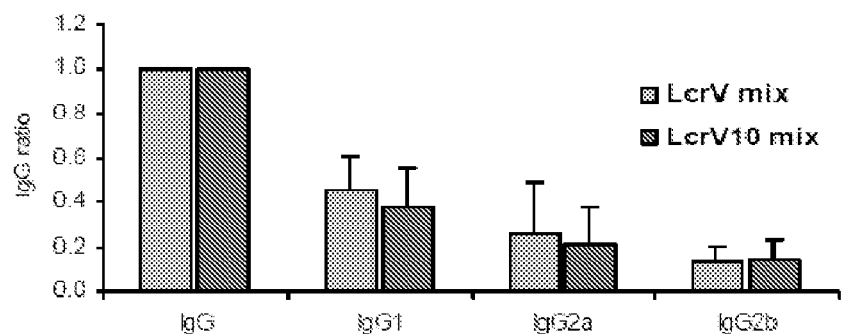
FIG. 7 shows the Th-1 type anti-PA IgG subclass pattern in mice immunized with the trivalent mucosal vaccine.
Figure 7:
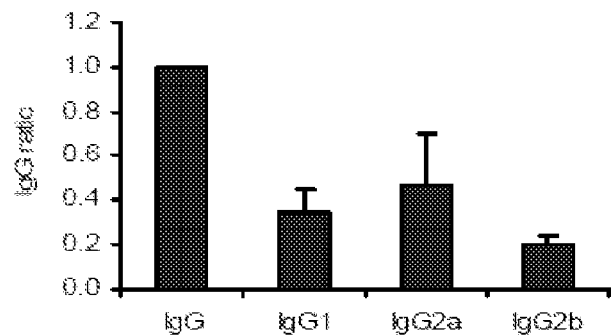
Figure 7:
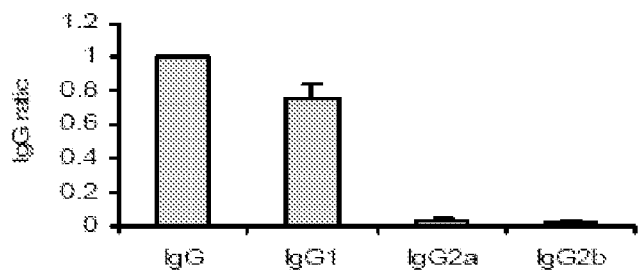
Figure 8:
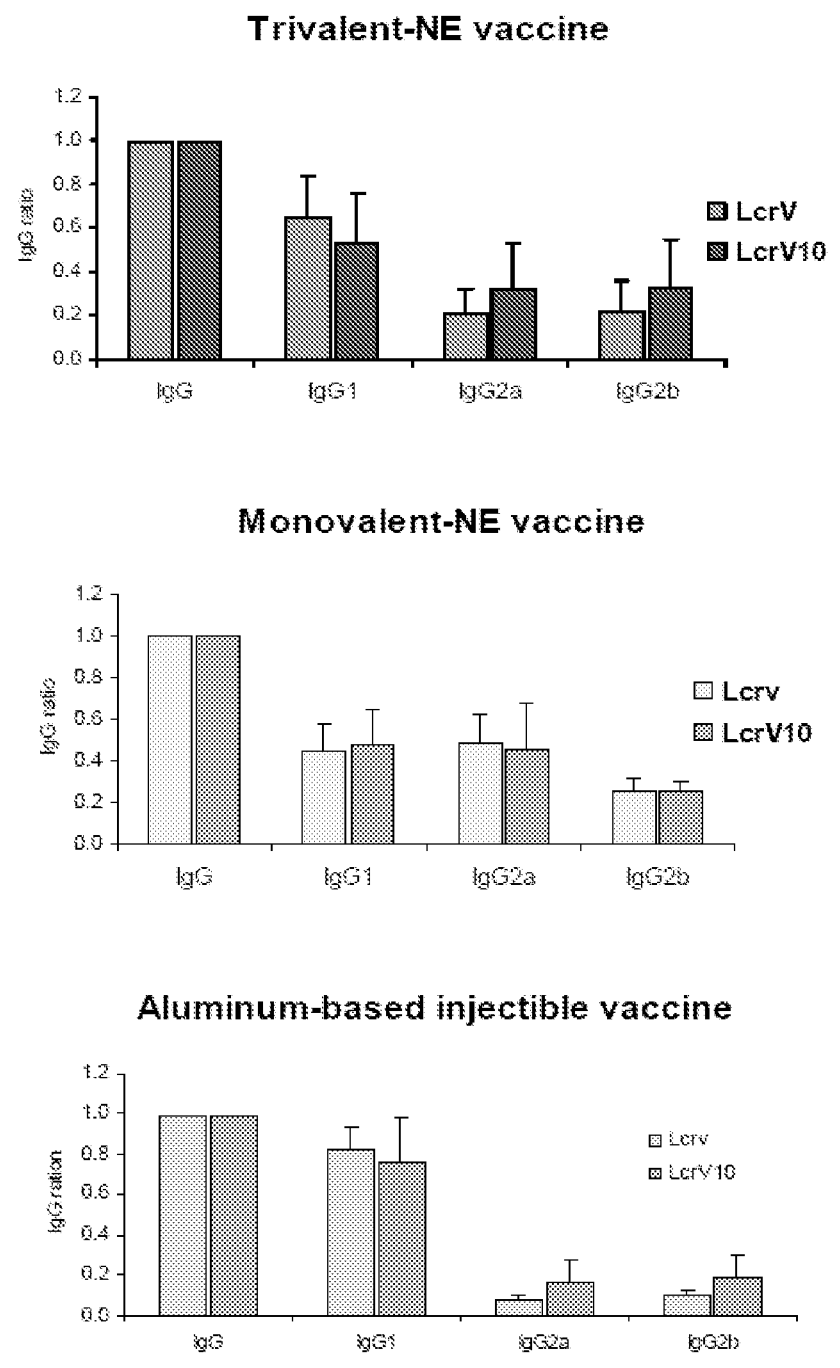
Figure 9:
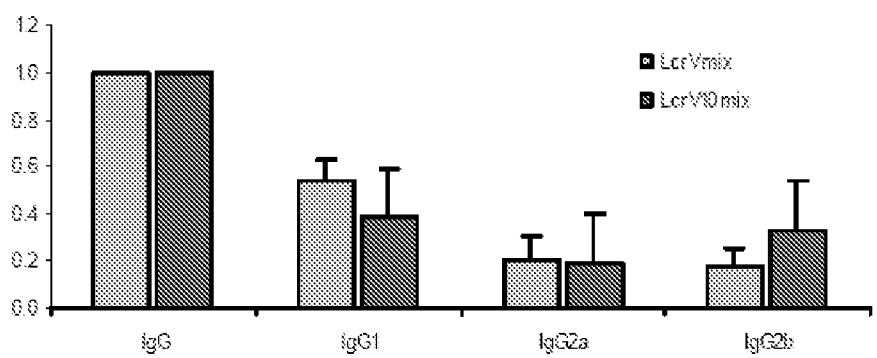
FIG. 9 shows Th-1 type anti-HCR/A1 subclass pattern in mice immunized with the trivalent mucosal vaccine.
Figure 9:
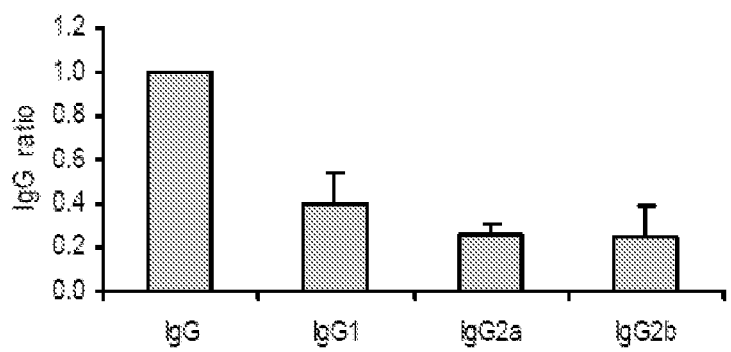
Figure 9:
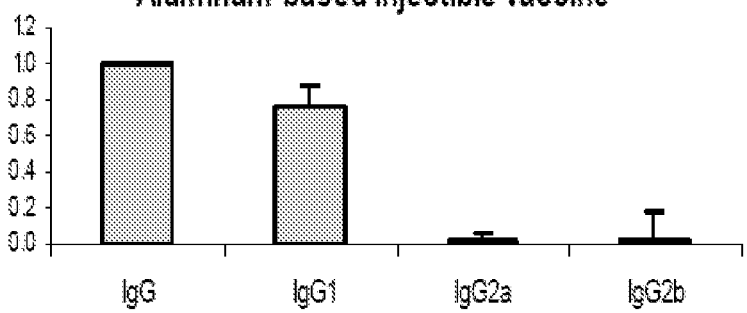

Analysis of IgG subclass in serum after nasal immunizations with a trivalent vaccine of the invention is shown in FIGS. 7-9. FIG. 7 shows that the analysis of IgG subclass in serum after nasal immunizations with NE adjuvanted trivalent vaccines indicated increased level of IgG2a and IgG2b anti-PA subclass antibodies in contrast to aluminum-based IM immunization that had a prevalence of IgG1 subclass of anti-PA IgG. Results presented as ratio of IgG subclass to total IgG titer. The elevated levels of IgG2 subclass antibodies indicated the induction of Th-1 polarization—in contrast to Th-2 type in aluminum based vaccine.

FIG. 8 shows anti-LcrV and mutant LcrV10 IgG subclass pattern. Distribution of IgG1, IgG2a and IgG2b in mice immunized with nasal administration of trivalent [HCR/A1-LcrV-PA]-NE or [HCR/A1-LcrV10-PA]-NE, nasal monovalent LcrV-NE or LcrV10-NE and intramuscular injection of aluminum-adsorbed LcrV or LcrV10. Nasal immunizations with NE adjuvant produced increased level of IgG2a and IgG2b subclass antibodies to both full length and deletion mutant of LcrV antigen in comparison to aluminum-based IM immunization with prevalence of IgG1 subclass of anti-LcrV and V10 IgG. Results presented as ratio of IgG subclass to total IgG titer.

FIG. 9 shows that similar IgG subclass patterns were detected for HCR/A1 botulism toxin in both LcrV and V10 protein mixes. Results presented as ration of IgG subclass to total IgG titer.

Mucosal immunization with NE-based vaccine produced antibody repertoire capable of recognizing LcrV epitopes similar to the natural pattern induced by surviving infection with *Y. pestis*. Loss of response to deleted regions of the full length protein resulting from immunization with the LcrV10 antigen was observed. Mucosal immunization with NE-based vaccines (trivalent or monovalent) produced antibodies capable of recognizing multiple regions of the PA protein. Frequency of the epitope recognition suggests binding to the pore formation regions of domain II and significant recognition of domains III and IV, especially enhanced in the receptor binding domain IV. LF/EF binding epitopes were recognized more frequently with serum from the monovalent rPA-NE vaccine. Thus, the present invention provides that NE based vaccine formulations maintain recognition of critical epitopes for protective immunity.

Figure 12:
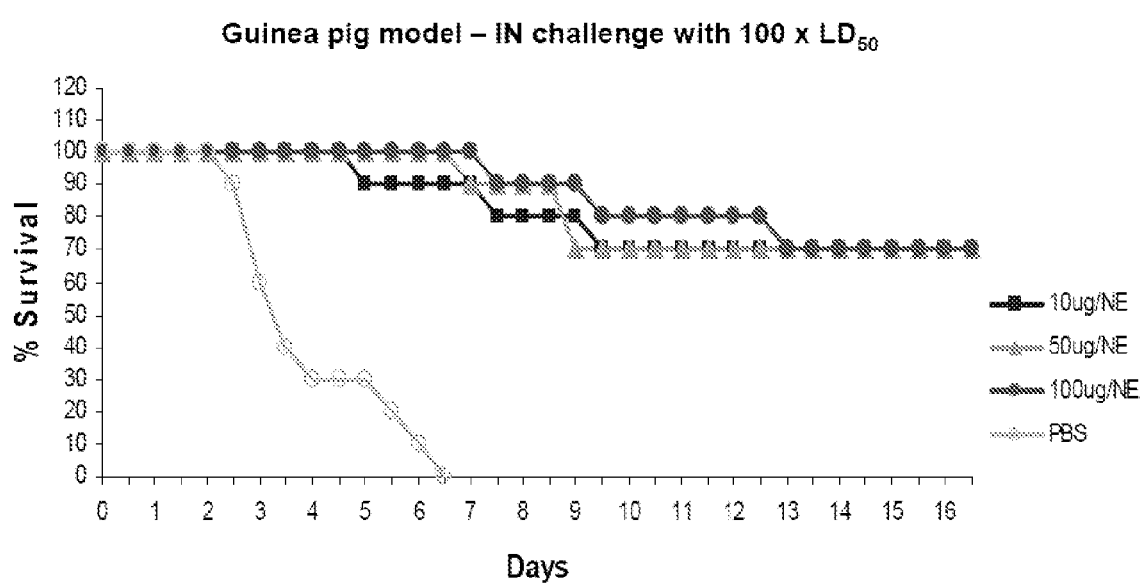
FIG. 12 shows protective immunity generated in a subject administered an intranasal trivalent vaccine of the invention against challenge with *B. anthracis* Ames spores.

Nasal immunization with NE-based trivalent vaccine produced protective immunity against challenge with live pathogens (See FIGS. 10-12). For example, as shown in FIG. 10, vaccination with 20 µg of either LcrV or LcrV10 protein in 20% NE produced 90% protection against 150×LD50 challenge with a virulent strain of plague and is comparable to intramuscular vaccination based on alum. Using lower concentration of NE adjuvant produced lower protective immunity-70%. FIG. 11 shows that vaccination with lower doses containing 10 µg of either protein in 20% NE produced 65 to 75%, while using 5% of NE resulted in 50 to 60% survival. Thus, the present invention provides a trivalent vaccine that provides protective immunity against challenge with the plague causing pathogen *Yersinia pestis*.

Nasal immunization with NE-based trivalent vaccine produced protective immunity against challenge with anthrax spores. Guinea pigs were immunized with 10 to 100 µg doses of PA protein and intranasally challenged with 100×LD50 of anthrax Ames spores. As shown in FIG. 12, survival in all groups was 70%—but higher doses of antigen produced increased time to death. Thus, the present invention provides a trivalent vaccine that provides protective immunity against inhalation challenge with anthrax spores.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of inducing an immune response in a subject, comprising: a) providing a multivalent immunogenic composition comprising: i) a nanoemulsion comprising:
   1) 30-90%, 60-80%, or 60-70% by volume oil;
   2) 3-15% by volume solvent, wherein said solvent is selected from the group consisting of ethanol and glycerol;
   3) 3-15% by volume surfactant, wherein said surfactant is selected from the group consisting of polyoxyethylenesorbitan monolaurate and polyoxyethylenesorbitan monooleate;
   4) cetylpyridinium chloride (CPC); and
   5) water; and
   ii) a plurality of different immunogens consisting of *Bacillus anthracis* immunogens, *Clostridium botulinum* immunogens, and *Yersinia pestis* immunogens, wherein said *Yersinia pestis* immunogens are LcrV or LcrV10; and b) administering said multivalent immunogenic composition to said subject under conditions such that said multivalent immunogenic composition concurrently induces a *Bacillus anthracis*-specific immune response, a *Clostridium botulinum*-specific immune response, and a *Yersinia pestis*-specific immune response in said subject.

2. The method of claim 1, wherein said administering comprises contacting a nasal mucosal surface of said subject with said multivalent immunogenic composition.

3. The method of claim 1, wherein said immunogens are selected from the group consisting of inactivated pathogen, isolated protein or peptide, purified protein or peptide, and recombinant protein or peptide.

4. The method of claim 1, wherein said plurality of different immunogens comprise protective antigen of *Bacillus anthracis*, rHCR/A1 of *Clostridium botulinum*, rLcrV protein of *Yersinia pestis*, or rLcrV10 protein of *Yersinia pestis*.

5. The method of claim 1, wherein said immune response comprises increased expression of IFN-γ in said subject.

6. The method of claim 1, wherein said immune response comprises a systemic IgG response specific to each of the different immunogens.

7. The method of claim 1, wherein said immune response comprises a mucosal IgA response specific to each of the different immunogens.

8. The method of claim 1, wherein said plurality of different immunogens are recombinantly produced.

9. The method of claim 1, wherein said plurality of different immunogens are protective antigen of *Bacillus anthracis*, rHCR/A1 of *Clostridium botulinum*, and rLcrV protein of *Yersinia pestis*.

10. The method of claim 1, wherein said plurality of different immunogens are protective antigen of *Bacillus anthracis*, rHCR/A1 of *Clostridium botulinum*, and rLcrV10 protein of *Yersinia pestis*.

11. The method of claim 1, wherein the immunogenic composition does not contain a mercury based preservative.

12. The method of claim 1, wherein said nanoemulsion comprises polyoxyethylene (20) sorbitan monooleate, ethanol, cetylpyridinium chloride (CPC), oil, and water.

13. The method of claim 1, wherein said nanoemulsion comprises polyoxyethylene (20) sorbitan monolaurate (TWEEN 20), ethanol, cetylpyridinium chloride (CPC), oil, and water.

14. The method of claim 1, nanoemulsion comprises about 5 vol. % of Polyoxyethylene (20) sorbitan monooleate, about 8 vol. % of ethanol, about 1 vol. % of cetylpyridinium chloride (CPC), about 64 vol. % of soybean oil, and about 22 vol. % of deionized water.

15. The method of claim 1, wherein said immunogenic composition comprises between 1 and 500 µg of each different immunogen.

16. The method of claim 1, wherein said immunogenic composition comprises between 2 and 75 µg of each different immunogen.

17. The method of claim 1, wherein said immunogenic composition comprises 20 µg of each different immunogen.

18. The method of claim 1, wherein said immunogenic composition comprises between 0.5 and 50% nanoemulsion.

19. The method of claim 1, wherein said immunogenic composition comprises about 20% nanoemulsion.

* * * * *

UNITED STATES PATENT AND TRADEMARK OFFICE
CERTIFICATE OF CORRECTION

PATENT NO. : 8,877,208 B2  
APPLICATION NO. : 12/472218  
DATED : November 4, 2014  
INVENTOR(S) : James R. Baker, Jr. et al.

Page 1 of 1

It is certified that error appears in the above-identified patent and that said Letters Patent is hereby corrected as shown below:

In the Claims

Claim 16 at column 81, line 7-9 of the patent reads:

16. The method of claim 1, wherein said immunogenic composition comprises between 2 and 75 µg of each different immunogen.

However, it should read:

16. The method of claim 1, wherein said immunogenic composition comprises between 5 and 75 µg of each different immunogen.

Signed and Sealed this  
Third Day of March, 2015

Michelle K. Lee  
*Deputy Director of the United States Patent and Trademark Office*